(12) United States Patent
Kaga et al.

(10) Patent No.: US 8,508,102 B2
(45) Date of Patent: Aug. 13, 2013

(54) PIEZOELECTRIC SENSOR

(75) Inventors: Shigetaka Kaga, Saitama (JP); Morio Onoe, Tokyo (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 0 days.

(21) Appl. No.: 13/481,868

(22) Filed: May 28, 2012

(65) Prior Publication Data
US 2012/0306315 A1     Dec. 6, 2012

(30) Foreign Application Priority Data

May 31, 2011  (JP) .................... 2011-122539
Oct. 13, 2011  (JP) .................... 2011-225844

(51) Int. Cl.
*H03H 9/25*  (2006.01)
(52) U.S. Cl.
USPC ........................ 310/313 A; 310/333
(58) Field of Classification Search
USPC .............. 310/313 R, 333, 313 A–313 D, 320, 310/321, 311, 367, 366, 331; 333/189, 193–196
IPC ........................................................ H03H 9/25
See application file for complete search history.

(56) References Cited

U.S. PATENT DOCUMENTS

| | | | | |
|---|---|---|---|---|
| 7,098,758 B2 * | 8/2006 | Wang et al. | .................... | 333/189 |
| 8,176,784 B2 * | 5/2012 | Onoe | ........................ | 310/313 D |
| 8,237,329 B2 * | 8/2012 | Onoe | ........................... | 310/320 |
| 8,242,664 B2 * | 8/2012 | Onoe | ........................... | 310/320 |

FOREIGN PATENT DOCUMENTS

JP   3885785   2/2007

OTHER PUBLICATIONS

Ivan V. Anisimkin, "New type of an acoustic plate mode: quasi-longitudinal normal wave", Ultrasonics, Aug. 2004, pp. 1095-1099, vol. 42, No. 10.
Onoe et al., "Analytical Study of Anisimkin's (Quasilongitudinal) Modes in Piezoelectric Plate", Frequency Control Symposium (FCS), 2010 IEEE International, Jun. 1-4, 2010, pp. 584~589.

* cited by examiner

*Primary Examiner* — Thomas Dougherty
*Assistant Examiner* — Karen B Addison
(74) *Attorney, Agent, or Firm* — Jianq Chyun IP Office

(57) ABSTRACT

A piezoelectric plate in the piezoelectric sensor is obtained from a rotated Y-plate where a rotation angle around the X-axis is set according to a type of the piezoelectric crystalline material, a detection region is located on a surface parallel to an X-Z plane, and a transmitting and a receiving parts are opposite to each other at positions sandwiching the detection region along an X-axis direction of the piezoelectric plate. When a guided wave excited by applying a frequency signal from the transmitting part satisfies $\xi h = m\pi/(2\lambda)$ (2h: thickness of the piezoelectric plate, $\xi$: wave number in the X-axis, $\lambda$: wave number in thickness direction normalized by $\xi$, m: positive even number), the rotation angle satisfies the displacement of a P wave component of the guided wave becomes the maximum, or the displacement of the SH wave component of the guided wave becomes the maximum.

16 Claims, 18 Drawing Sheets

PIEZOELECTRIC SENSOR

CROSS-REFERENCE TO RELATED APPLICATION

This application claims the priority benefit of Japan application serial no. 2011-225844, filed on Oct. 13, 2011, and claims the priority benefit of a Japan application serial no. 2011-122539, filed on May 31, 2011. The entirety of each of the above-mentioned patent applications is hereby incorporated by reference herein and made a part of this specification.

FIELD OF THE INVENTION

The present invention relates to a technology for sensing a to-be-sensed object or detecting a viscosity change of a fluid by using QL mode (quasilongitudinal mode) and QS mode (quasishear mode).

BACKGROUND OF THE INVENTION

Anisimkin discovered numerically and verified experimentally a quasilongitudinal mode (below describe as "QL mode"), which is a special propagation mode to propagate along X-axis direction in a quartz ST cut (non-patent document 1).

Considering a guided wave propagated in a plate that consists of an anisotropy crystalline material and assuming that a longitudinal wave component is a P wave component, a transverse wave component having a displacement vertical to a surface of the plate is an SV wave component and a transverse wave component having a displacement parallel to the above-mentioned surface is an SH wave component, the above-mentioned QL mode has the features, such as (i) there is only the P wave component on the surface of the plate, (ii) inside the plate as well, the P wave component is larger than the SV wave and the SH wave components. Specially, the feature of (i) is suitable for applying to a piezoelectric sensor, which uses a piezoelectric crystalline material for sensing an adsorption of a to-be-sensed object to a piezoelectric plate surface or detecting a viscosity change of a fluid contacting with the piezoelectric plate surface.

The inventors analyzed conditions that the QL mode and a quasishear mode (below described as "QS mode") are excited for quartz plates, wherein the QS mode is which the P wave component becomes zero and the SH component and the SV component remain on the surface of the plate (non-patent document 2). For further improvement in sensitivity and energy efficiency of the piezoelectric sensor using these QL and QS modes, a piezoelectric crystalline material with high oscillatory frequency in the same plate thickness and high electromechanical coupling factor is required.

In the patent document 1, a surface acoustic wave device to excite a quasilongitudinal type leaky surface acoustic wave on the quartz plate by using an IDT electrode is disclosed. However, the QL mode and the QS mode are bulk waves (lamb waves), in which the P wave component, etc., is excited inside the plate as well; therefore, it is different from the technique in the patent document 1 which uses the surface acoustic wave. In addition, in the patent document 1, there is no description about any piezoelectric sensor for detecting a viscosity of a to-be-sensed object or a fluid.

PRIOR ART REFERENCE

Patent Document

Patent document 1: Japanese Patent No. 3885785
Non-patent document 1: "New type of an acoustic plate mode: quasi-longitudinal normal wave", Ultrasonics, vol. 42, No. 10, pp. 1095-1099, 2004
Non-patent document 2: "Analytical Study of Anisimkin's (Quasilongitudinal) Modes in Piezoelectric Plate", Proc. IEEE Intern. Freq. Control. Symp., pp. 584-589, 2010

SUMMARY OF THE INVENTION

The invention was made under the following conditions, and the purpose of the invention is to provide a piezoelectric sensor with high sensitivity and high energy conversion efficiency.

According to an embodiment, a piezoelectric sensor is provided, the piezoelectric sensor comprises, a piezoelectric plate, a detection region, a transmitting part and a receiving part. The piezoelectric plate obtained from a rotated Y-plate having a rotation angle θ around an X-axis, wherein when at least a two-fold symmetry axis, or a symmetry axis of a piezoelectric crystalline material having a mirror symmetry plane is set as the X-axis, the rotation angle θ is set according to the type of the piezoelectric crystalline material. The detection region is located on a surface parallel to an X-Z plane of the piezoelectric plate. The transmitting part and the receiving part are located along a direction of the X-axis of the piezoelectric plate and opposite to each other at positions that sandwiches the detection region. When a guided wave excited on the piezoelectric plate by applying a frequency signal from the transmitting part meets the following equation (A), the rotation angle θ satisfies (a1) the guided wave propagating in the X-axis direction inside the piezoelectric plate has a P wave component, an SV wave component and an SH wave component, and (b1) when a displacement of the P wave component is $u_1$, a displacement of the SV wave component is $u_2$ and a displacement of the SH wave component is $u_3$, the displacement $u_1$ becomes the maximum and the displacements $u_2$ and the $u_3$ become less than 10% of the displacement $u_1$ on the surface.

$$\xi h = m\pi/(2\lambda) \tag{A}$$

where 2h: a plate thickness of the piezoelectric plate, ξ: a wave number in the X-axis direction, λ: a wave number in a plate thickness direction normalized by ξ, m: positive even number.

According to another embodiment, a piezoelectric sensor is provided, and the piezoelectric sensor comprises a piezoelectric plate, a detection region, a transmitting part and a receiving part. The piezoelectric plate is obtained from a rotated Y-plate having a rotation angle θ around an X-axis, wherein when at least a two-fold symmetry axis, or a symmetry axis of the piezoelectric crystalline material having a mirror symmetry plane is set as the X-axis, the rotation angle θ is set according to a type of the piezoelectric crystalline material. The detection region is located on a surface parallel to an X-Z plane of the piezoelectric plate. The transmitting part and the receiving part are located along a direction of the X-axis of the piezoelectric plate and opposite to each other at positions that sandwiches the detection region. When a guided wave excited on the piezoelectric plate by applying a frequency signal from the transmitting part meets the following equation (B), the rotation angle θ satisfies (a2) the guided wave propagating in the X-axis direction of the piezoelectric plate has a P wave component, an SV wave component and an SH wave component, (b2) when a displacement of the P wave component is $u_1$, a displacement of the SV wave component is $u_2$ and a displacement of the SH wave component is $u_3$, the displacement $u_3$ becomes maximum and the displacement $u_1$ becomes less than 10% of the displacement $u_3$ on the surface.

$$\xi h = m\pi/(2\lambda) \tag{B}$$

where 2h: a plate thickness of the piezoelectric plate, $\xi$: a wave number in the X-axis direction, $\lambda$: a wave number in a plate thickness direction scaled with $\xi$, m: positive odd number.

Each of the above-mentioned piezoelectric sensors may include the following features:

(a) The transmitting part and the receiving part are IDT electrodes, in which an electrode finger pitch d is defined by the following equation (C):

$$d = (2\pi h/(\xi h))/4 \tag{C}$$

(b) The piezoelectric crystalline material is lead zirconate titanate.

(c) The piezoelectric crystalline material is lithium niobate.

(d) The piezoelectric crystalline material is selected from a group of langasite-type piezoelectric crystalline materials consisting of Al-substituted langatate, langatate, langasite or langanite.

(e) The piezoelectric crystalline material is gallium phosphate.

(f) The piezoelectric sensor is a sensing sensor in which an adsorption layer to adsorb a sensing object is disposed on the detection region.

(g) The piezoelectric sensor is a viscosity sensor for detecting a viscosity change of a fluid contacting with the detection region.

According to the invention, comparing with a QCM using an AT-cut crystal, the piezoelectric sensor is constructed by using the QL mode or the QS mode, which can be excited at higher frequency with the same plate thickness, so that the piezoelectric sensor with high sensitivity can be obtained. In addition, by using a piezoelectric material with high electromechanical coupling factor, the piezoelectric sensor with high energy efficiency can be obtained.

DESCRIPTION OF EMBODIMENTS

Excitation Conditions

Excitation conditions of QL mode (quasilongitudinal mode) and QS mode (quasishear mode) for a piezoelectric crystalline material are shown. A piezoelectric sensor 1 according to the embodiment of the invention comprises a piezoelectric plate 10 for propagating a guided wave in the X-axis direction of a rotated Y-plate.

When assuming that a displacement of a P wave, which is a longitudinal wave component of the guided wave propagating in the above-mentioned piezoelectric plate 10, is u1, a displacement of an SV wave, which is a transversal wave component having a displacement vertical to a surface of the piezoelectric plate 10, is u2 and a displacement of an SH wave, which is a transversal wave component having a displacement parallel to the above-mentioned surface, is $u_3$, the guided wave is represented by the following equations (1) and (2).

Figure 1:
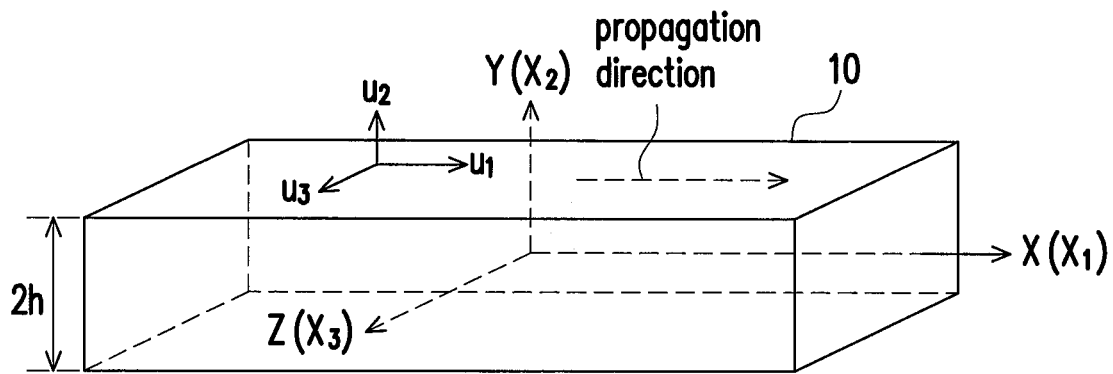
FIG. 1 is a schematic diagram of a piezoelectric plate for propagating a guided wave in QL mode and QS mode along X-axis direction.

Equation (1)

$$u_i = A_i \exp j(\lambda \xi x_2) \exp j(\xi x_1 - \omega t) \tag{1}$$

wherein $u_i$ is a displacement in i (=1, 2, 3) direction shown in FIG. 1, $A_i$ is an amplitude ratio of a displacement of a wave corresponding to $\lambda_i$; $\lambda$ is a wave number in a plate thickness direction normalized by $\xi$, $\xi$ is a wave number in the X-axis direction, $x_2$ is a coordinate in Y-axis direction, $x_1$ is a coordinate in the X-axis direction, and $\omega$ is an angular frequency.

Equation (2)

$$\phi_n = A_4 \sqrt{\frac{\varepsilon_{11}}{c_{11}}} \exp j(\lambda \xi x_2) \exp j(\xi x_1 - \omega t) \quad (2)$$

wherein, $\phi_n$ is a dimensionless electric potential, $\in$ is a dielectric constant, and c is stiffness.

On the other hand, a piezoelectric basic equation in the piezoelectric plate 10 is represented by the following equation (3), which is normalized by equations (4)~(7), and a determinant (8) has to be zero in order to satisfy an equation of motion and an equation of a quasi-electrostatic field.

Equation (3)

$$\begin{bmatrix} [T] \\ [D] \end{bmatrix} = M * \begin{bmatrix} [S] \\ [E] \end{bmatrix} \quad (3)$$

Equation (4)

$$[M] = \begin{bmatrix} [c] & -[e]^T \\ [e] & [\varepsilon] \end{bmatrix} \quad (4)$$

Equation (5)

$$[c_n] = \frac{1}{c_{11}} [c] \quad (5)$$

Equation (6)

$$[\varepsilon_n] = \frac{1}{\varepsilon_{11}} [\varepsilon] \quad (6)$$

Equation (7)

$$[e_n] = \frac{1}{\sqrt{c_{11}\varepsilon_{11}}} [e] \quad (7)$$

Equation (8)

$$det(\Gamma A(\lambda)) = 0 \quad (8)$$

$\Gamma A(\lambda)$ in the equation (8) is represented by the following equation (9).

Equation (9)

$$\Gamma A(\lambda) = \begin{bmatrix} 1 & 0 & 0 & 0 & 0 & \lambda & 0 & 0 & 0 \\ 0 & \lambda & 0 & 0 & 0 & 1 & 0 & 0 & 0 \\ 0 & 0 & 0 & \lambda & 1 & 0 & 0 & 0 & 0 \\ 0 & 0 & 0 & 0 & 0 & 0 & 1 & \lambda & 0 \end{bmatrix} * Mn * \begin{bmatrix} 1 & 0 & 0 & 0 \\ 0 & \lambda & 0 & 0 \\ 0 & 0 & 0 & 0 \\ 0 & 0 & \lambda & 0 \\ 0 & 0 & 1 & 0 \\ \lambda & 1 & 0 & 0 \\ 0 & 0 & 0 & 1 \\ 0 & 0 & 0 & \lambda \\ 0 & 0 & 0 & 0 \end{bmatrix} - \begin{bmatrix} C_{pn}^2 & 0 & 0 & 0 \\ 0 & C_{pn}^2 & 0 & 0 \\ 0 & 0 & C_{pn}^2 & 0 \\ 0 & 0 & 0 & C_{pn}^2 \end{bmatrix} \quad (9)$$

In the equation (9), $C_{pn}$ is a phase velocity normalized by with a longitudinal wave velocity, and is represented by the following equations (10) and (11).

Equation (10)

$$C_{pn} = \frac{\omega}{\xi} \frac{1}{V_L} \quad (10)$$

Equation (11)

$$V_L = \sqrt{\frac{c_{11}}{\rho}} \quad (11)$$

wherein, $\rho$ is a density of the piezoelectric plate 10, and VL is a sound velocity of the longitudinal wave (P wave component) of the piezoelectric plate 10.

Generally, equation (9) is an eighth degree equation of $\lambda$; however, as mentioned above, when at least a two-fold symmetry axis and a mirror plane (Y-Z plane) of the piezoelectric crystalline material is selected as the X-axis, equation (9) becomes a quadratic equation of $\lambda$. As a result, four roots are determined and the amplitude ratios $A_i$ are determined correspondingly. Equations (1) and (2) become the sum of the four terms having coefficients corresponding to the roots and the coefficients are determined by a boundary condition.

A mechanical boundary condition is free on a surface (x2=±h) of the piezoelectric plate 10, and the following equation (12) can be established for a stress T.

Equation (12)

$$T_2 = T_4 = T_6 = 0 \quad (12)$$

In addition, for an electrical boundary condition, if there is no electrode, the following equation (13) can be established for an electric displacement.

Equation (13)

$$D_2 = 0 \quad (13)$$

On the other hand, if there is an electrode, the following equation (14) can be established for an electrical potential.

Equation (14)

$$\phi = 0 \quad (14)$$

When the same boundary condition is adapted to the upper and lower surfaces of the piezoelectric plate 10, a central plane of the piezoelectric plate 10 is divided into a symmetric mode and an oblique symmetric mode. In addition, in order to satisfy the boundary conditions, a determinant obtained from the coefficients has to be zero. Hereby, a dispersion curve, illustrating a relationship between the frequency and $\xi h$ (wave number in the X-axis direction and half plate thickness), is provided.

Specially, the effect of piezoelectricity is small, except for a high-coupling piezoelectric material, so that a search at the first stage can be performed by ignoring the piezoelectricity and focusing on only the stiffness for the equation (8). At this time, equation (8) is represented by the following equation (15).

Equation (15)

$$\begin{bmatrix} c_{66}\lambda^2 + 1 - C_{pn}^2 & (c_{12}+c_{66})\lambda & (c_{14}+c_{56})\lambda \\ (c_{12}+c_{66})\lambda & c_{22}+c_{66}-C_{pn}^2 & c_{24}\lambda^2 + c_{56} \\ (c_{14}+c_{56})\lambda & c_{24}\lambda^2 + c_{56} & c_{24}\lambda^2 + c_{55} - C_{pn}^2 \end{bmatrix} \quad (15)$$

Equation (15) is a cubic equation of $\lambda^2$ and if the phase velocity is equal to the longitudinal wave velocity, the QL mode or the QS mode is excited when one root thereof becomes zero and roots of the remaining quadratic equation becomes multiple roots (non-patent document 2 in the background art).

A constant term of the above-mentioned cubic equation is represented by the following equation (16), and in equation (16), one root of equation (15) becomes zero when $C_{pn}=1$. In addition, whether the remaining two roots become multiple roots or not can be determined by a discriminant of the quadratic equation.

Equation (16)

$$[(c_{55}-C_{pn}^2)(c_{66}-C_{pn}^2)-c_{56}^2](1-C_{pn}^2) \quad (16)$$

In case of multiple roots, one of solutions of the equation (15) is represented by the following equation (17).

Equation (17)

$$\sin(\lambda\xi h)=0 \quad (17)$$

That is, when m is a positive even number in the following equation (18), a solution of equation (15) becomes multiplicity roots, and at this time, the displacement of the SV wave $u_2$ and the displacement of the SH wave $u_3$ on the surface of the piezoelectric plate 10 both become zero, and the QL mode is excited.

Equation (18)

$$\xi h = m\pi/(2\lambda) \quad (18)$$

In addition, the other solution in case that the equation (13) is multiple root is represented by the following equation (19).

Equation (19)

$$\cos(\lambda\xi h)=0 \quad (19)$$

In this case, when m is a positive odd number in the aforementioned equation (18), a solution of the equation (15) becomes multiple root. However, at this time, the displacement of the P wave $u_1$ on the surface of the piezoelectric plate 10 becomes zero. On the other hand, when the displacement of the SV wave $u_2$ and the displacement of the SH wave $u_3$ remain (a result obtained in which the displacement of the SV wave $u_2$ also becomes smaller and only the displacement of the SH wave $u_3$ becomes larger for LiNbO$_3$ and PZT5H), the QS mode is excited.

A frequency f and a wave length $\Lambda$ when exciting the QL mode and the QS mode are represented by the following equations (20) and (21).

Equation (20)

$$f = \frac{\xi h V_L}{2\pi h} \quad (20)$$

Equation (21)

$$\Lambda = \frac{2\pi h}{\xi h} \quad (21)$$

Piezoelectric Sensor

Figure 2:
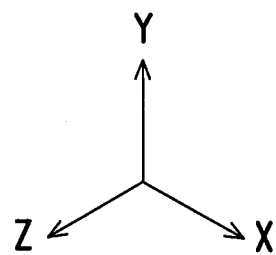
FIG. 2 is an exterior perspective view of a piezoelectric sensor with IDTs.
Figure 2:
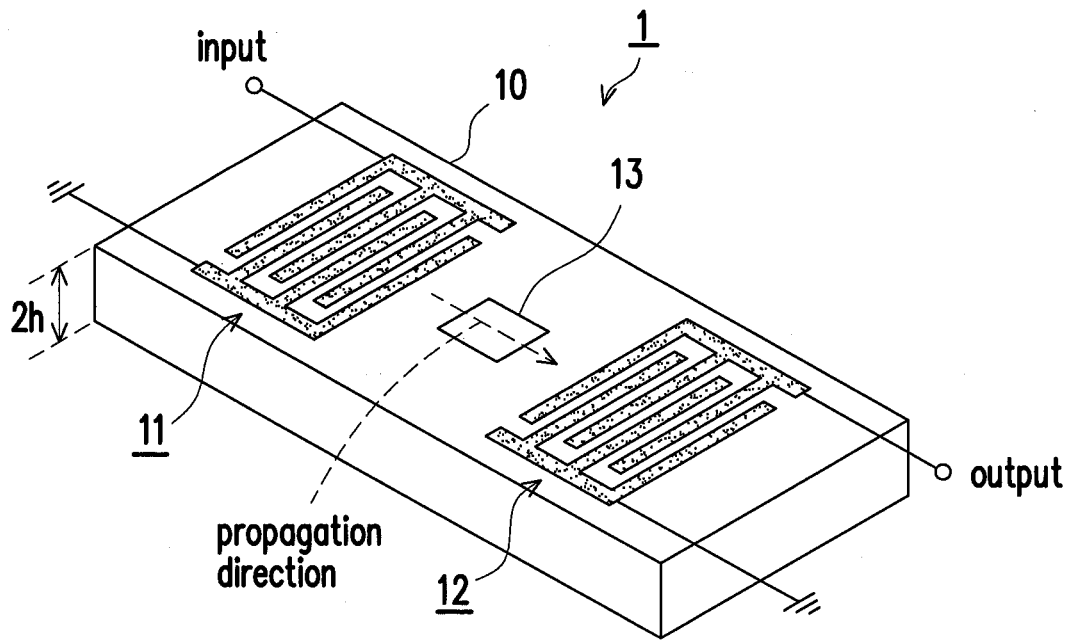

A configuration of the piezoelectric sensor 1 using the QL mode and the QS mode excited by the conditions described above will be described with reference to FIG. 2 and FIG. 3. As shown in the perspective view of FIG. 2, the piezoelectric sensor 1 has a structure in which two IDT (Inter Digital Transducer) electrodes (a first IDT electrode 11, a second IDT electrode 12) are formed on the surface of the piezoelectric plate 10 in a form of a small plate constructed by cutting the piezoelectric crystalline material in the predetermined direction, and a detection region 13 for detecting a detection object is located at a position sandwiched between these IDT electrodes.

The piezoelectric plate 10 is composed of a piezoelectric crystalline material, such as lithium niobate (below described as "LiNbO3"), PZT (registered trademark, a solid solution of lead zirconate (PbZrO3) and lead titanate (PbTiO3)) on which a poling process is performed in the c-axis direction, or crystal.

Moreover, when at least a two-fold symmetry axis of the above-mentioned piezoelectric crystalline material or a symmetry axis of a piezoelectric crystalline material having the mirror symmetry plane (rotation axis of the mirror symmetric plane for the mirror symmetry) is set as the X-axis, the piezoelectric plate 10 can be obtained from the rotated Y-plate and is processed into a small plate with a thickness of 2h, wherein the rotated Y-plate is formed by rotating a Y-plate around the X-axis with a rotation angle θ, and the Y-plate has a thickness in the Y-axis direction perpendicular to the X-axis. In the case of crystal system 32, the piezoelectric crystalline material, in which the X-axis is the two-fold symmetry, includes, for example, crystal, a langasite-type piezoelectric crystalline material and gallium phosphate (GaPO$_4$), etc. In the case of crystal system 3m, the piezoelectric crystalline material, in which the Y-Z plane is the mirror plane, includes, for example, lithium niobate (LiNbO$_3$) and lithium tantalite (LiTaO$_3$), etc.

To simplify the description below, it is assumed that a thickness direction of the rotated Y plate is Y-axis (the direction is different from the Y-axis before rotation), a propagation direction of the guided wave in the QL mode or the QS mode is X-axis, and a direction perpendicular to these X-axis and Y-axis is Z-axis.

The first and the second IDT electrodes 11 and 12 are formed on a surface at one side of the X-Z plane of the piezoelectric plate 10 to face each other along the propagation direction (X-axis direction) of the guided wave. Then, a region on the surface of the piezoelectric plate 10 sandwiched between the two IDT electrodes 11 and 12 becomes the detection region 13 for detecting, for example, an adsorption of a sensing object or a viscosity change of the fluid. A surface, at which the detection region 13 is located, is referred to as a principle surface of the piezoelectric sensor 1.

Among these IDT electrodes 11 and 12, the first IDT electrode 11 located on an upstream side of the propagation direction of the guided wave is served as a transmitting part to excite the guided wave in the QL mode or the QS mode by electromechanically converting an electrical signal inputted to the electrode 11. On the other hand, with the detection region 13 between the IDT electrodes 11 and 12, the second IDT electrode 12 is located on the downstream side of the propagation direction of the guided wave, and is served as a receiving part to take out an electrical signal by electromechanically converting the guided wave in the QL mode (or the QS mode) propagated in the piezoelectric plate 10.

Figure 3:
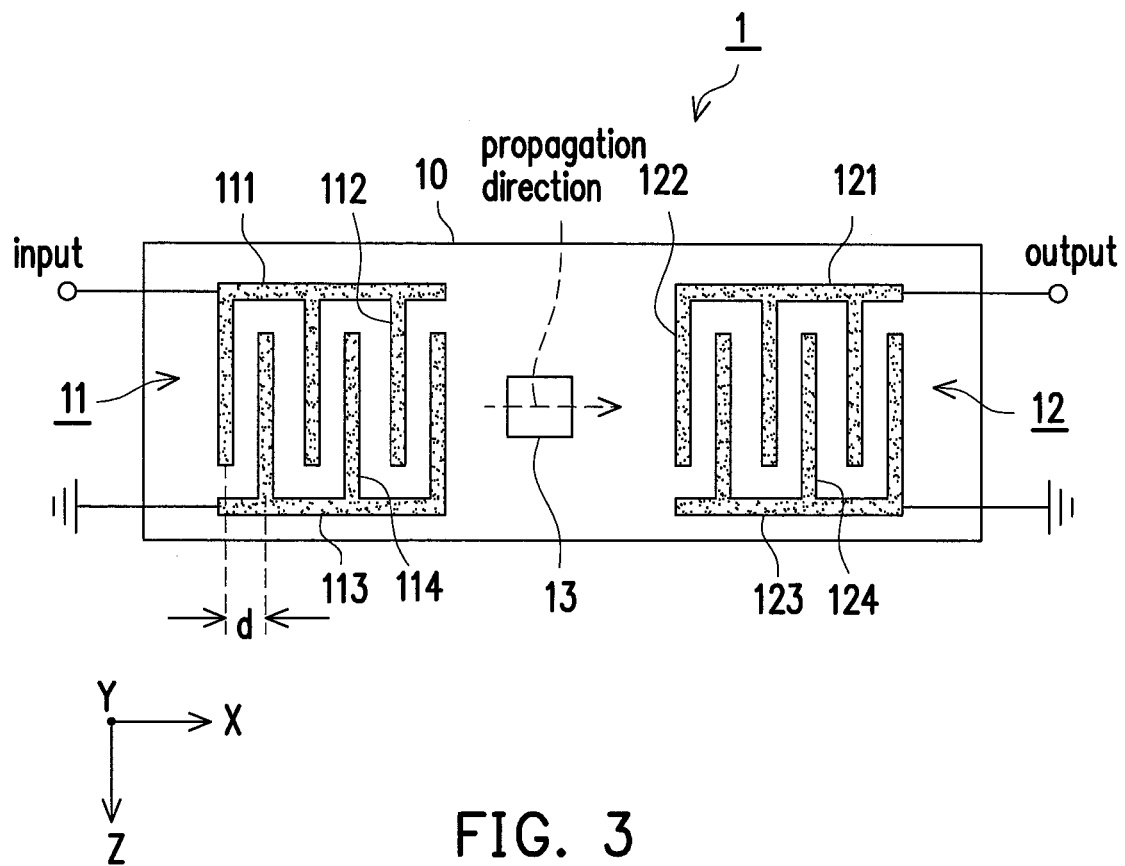
FIG. 3 is a plan view of the piezoelectric sensor.

Each of the IDT electrodes 11 and 12 have approximately the same structure as each other. Therefore, describing the structure of the first IDT electrode 11 as an example, the first IDT electrode 11, for example, is configured as the well-known IDT electrode consisting of a metal film, such as aluminium or gold. That is, as shown in FIG. 3, for two bus bars 111 and 113 disposed along the propagation direction of the guided wave, a plurality of electrode fingers 112 and 114 are connected in a shape of finger-interlacing type. For example, several dozens to several hundreds of the electrode fingers are formed in each of the IDT electrodes shown in the embodiment of the invention, however, the number is omitted in the figures.

According to the above-mentioned equation (21), a wave length of the guided wave in the QL mode or the QS mode excited on the piezoelectric plate 10 is determined by a half plate thickness h of the piezoelectric plate 10 and a wave number 4 in the X-axis direction ($\Lambda=(2\pi h)/(\xi h)$). In addition, as explained by using the equations (17)-(19), when the equation of motion deduced from the piezoelectric basic equation has multiple root, the QL mode or the QS mode is excited. Then, whether the equation of motion has multiple root or not is determined by a rotation angle θ around the X-axis on the rotated Y-plate, and the value of "ξh" at the time can be obtained by the equation (18) ($\xi h=m\pi/(2\lambda)$), QL mode when m is a positive even number, QS mode when m is a positive odd number).

Considering the circumstances mentioned above, by using the rotated Y-plate which is previously cut in a direction where the QL mode or the QS mode can be excited, a wave length of the guided wave excited by these modes is determined only by the thickness 2h of piezoelectric plate 10 and the value can be known in advance by using the equations (18) and (21).

Thus, by disposing the electrode fingers 112, 114 of the first IDT electrode 11 according to the wave length of the guided wave that propagates in the piezoelectric plate 10 and inputting the electrical signal having the frequency calculated by the equation (20) from the first IDT electrode 11, the guided wave in the QL mode or the QS mode having "ξh" corresponding to the piezoelectric crystalline material and the half plate thickness can be excited on the piezoelectric plate 10. More specifically, the guided wave in the pre-designed mode can be excited by disposing the electrode fingers 112, 114 alternately in a manner that an electrode finger pitch d between the electrode finger 112 connected to the bus bar 111 where the frequency signal is inputted and the electrode finger 114 connected to the grounded bus bar 113 can be ¼ of the wave length calculated by the equation (21).

On the other hand, the second IDT electrode 12 on the receiving side is excited by the first IDT electrode 11, and electrode fingers 122 connected to the bus bar 121 on the output side are disposed, for example, in positions where the inputted frequency signal and the phase are matched, so that a displacement of the guided wave propagating in the piezoelectric plate 10 becomes the maximum. Then, the above-mentioned electrode fingers 122 and electrode fingers 124 connected to a bus bar 123 on the ground side are disposed alternately so that the electrode finger pitch becomes d.

By such structure, the frequency signal inputted from the first IDT electrode 11 excites the QL mode or the QS mode through the electromechanical conversion, and the guided wave in the said mode propagates in the piezoelectric plate 10 to reach to the second IDT electrode 12 and is taken out as an electrical signal from the second IDT electrode 12 through the electromechanical conversion.

Then, when the detection region 13 is located on the surface of the piezoelectric plate 10 between the first IDT electrode 11 and the second IDT electrode 12, a state of the surface on the detection region 13 is changed, for example, by an adsorption of a sensing object or a viscosity change of the fluid contacting with the detection region 13. Thus, when the state of the surface on the detection region 13 is changed, the guided wave propagating in the piezoelectric plate 10 is affected by the change of the surface state and detected as a change of the frequency of the electrical signal outputted from the second IDT electrode 12.

Figure 4:
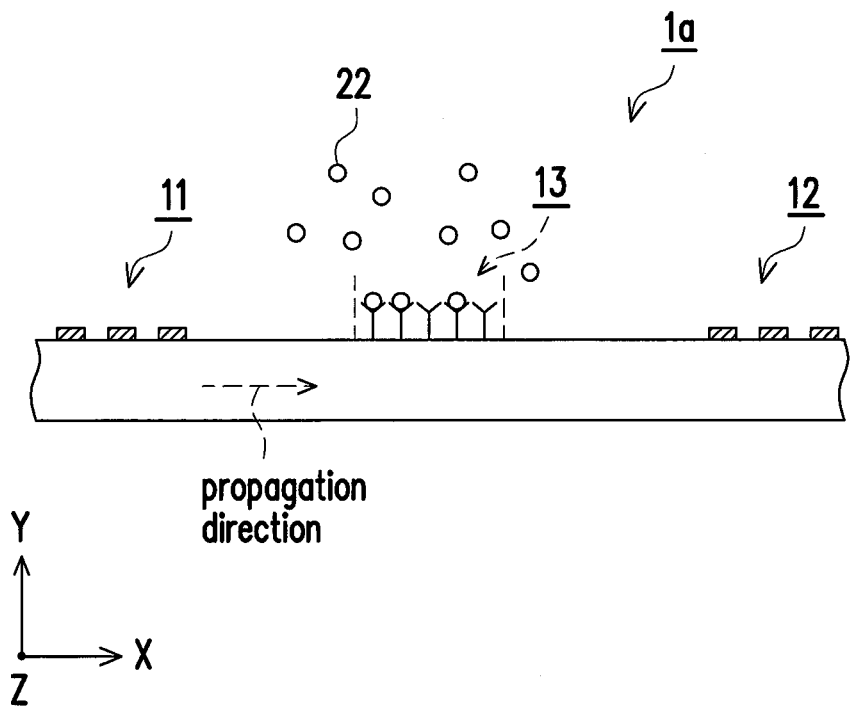
FIG. 4 is an application example for a sensing sensor to adsorb and sense a to-be-sensed object.

FIG. 4 is an application example for a sensing sensor 1a having an adsorption layer 21 to adsorb a sensing object 22 in the detection region 13 of the piezoelectric sensor 1 with the above-mentioned configuration. For example, when a specific antigen in blood or serum, etc., is sensed as the sensing object 22, an antibody which selectively reacts and bonds with the said sensing object 22, etc., is used as the adsorption layer 21. Then, when the sensing object 22 is adsorbed on the adsorption layer 21, due to a change of the surface state, for example, a change of the sound velocity $V_L$ (equation (11)) of the P wave component propagating on the surface of the piezoelectric plate 10, a state of the guided wave propagating in the piezoelectric plate 10 is changed, and detected as a change of the frequency of the electrical signal outputted from the second IDT electrode 12. Then, by using a calibration curve to indicate a corresponding relationship between a change amount of the frequency and an adsorption amount of the sensing object 22, etc., the adsorption amount of the sensing object 22 can be specified from the change amount of the frequency.

Figure 5:
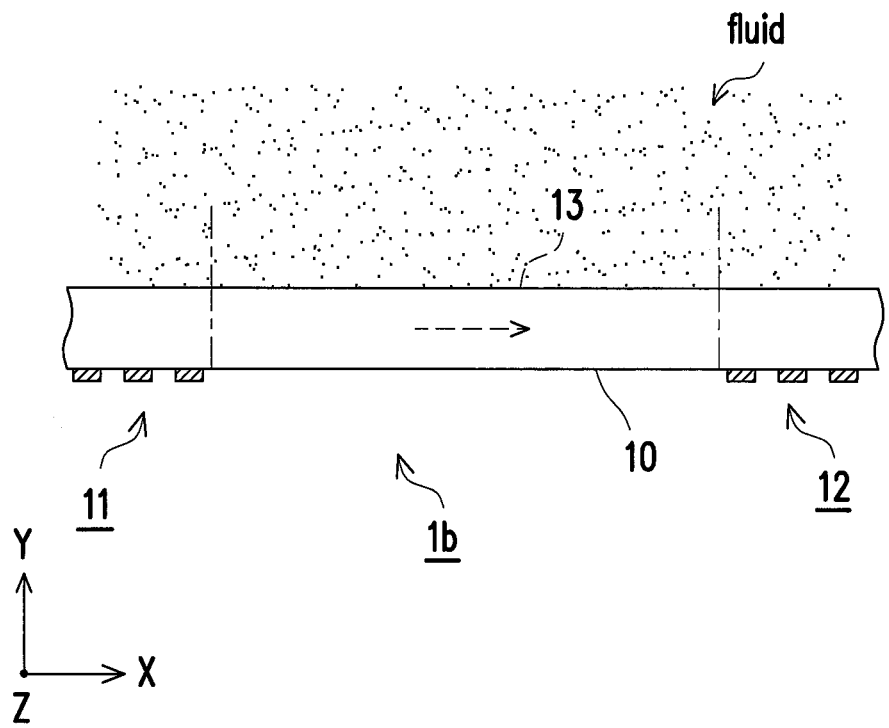
FIG. 5 is an application example for a viscosity sensor to detect a viscosity change of a fluid.

In addition, different from the case of SAW, since the QL mode and the QS mode excited on the piezoelectric plate 10 are bulk waves, the detection region 13 may be located serving a surface opposite to the surface which the IDT electrodes 11, 12 are located as a main surface. FIG. 5 is an application example for a viscosity sensor 1b, which is constructed in a manner that the fluid is in contact with a surface opposite to the surface where the IDT electrodes 11, 12 are formed, and the surface contact with the fluid serves as the detection region 13 (principle surface). In this case as well, the detection region 13 is located at a position sandwiched between the IDT electrodes 11 and 12, which are located on the opposite surface to the principle surface.

In the viscosity sensor 1b, when a viscosity of the fluid contacting with the detection region 13 is changed, a propagation state of the guided wave propagating on the principle surface of the piezoelectric plate 10 is changed, and the change may affect the propagation state of the guided wave on the surface opposite to the surface where the IDT electrodes 11, 12 are located. As a result, a viscosity change of the fluid contacting with the detection region 13 is detected as a frequency change of the electrical signal, which is acquired from the second IDT electrode 12. Then, for example, by referring a calibration curve for indicating a relationship between a viscosity of the fluid and a change of the frequency from atmosphere, etc., a viscosity of the fluid can be obtained.

With the structure of the piezoelectric sensor, an oscillation frequency in the QL mode calculated from equation (20) is compared with an oscillation frequency in an energy trapping resonator of the AT-cut crystal conventionally used for QCM. For example, when it is assumed that the half plate thickness of the piezoelectric plate 10 is h=100 μm, an oscillation frequency of the AT-cut crystal is 8.35 MHz. In contrast, the oscillation frequency for LiNbO$_3$ (κ=114°, ξh=2.39) is 25.2 MHz, and for PZT (in PZT5H, θ=73.12° or 10.88°, ξh=1.48) is 9.7 MHz. In either material, an oscillation frequency higher than that of the AT-cut crystal is obtained for the same plate thickness.

In addition, for Al-substituted langatate (composition ratio La$_3$Ta$_{0.5}$Ga$_{5.3}$Al$_{0.2}$O$_{14}$, below described as LTGA), langatate (langasite-type crystalline material including La, Ta, Ga, below described as LGT), langasite (langasite-type crystalline material including La, Ga, Si, below described as LGS), langanite (langasite-type crystalline material including La, Nb, Ga, below described as LGN), and gallium phosphate (GaPO$_4$), which are langasite-type piezoelectric crystalline materials other than LiNbO$_3$ and PZT, a set of rotation angle θ around the above-mentioned X-axis and ξh and an oscillation frequency at that time are calculated. As a result, for example, LTGA is 17.8 MHz in the QL mode (m=2) when θ=116° and ξh=2.02, LGT is 17.5 MHz in the QL mode (m=2) when ξh=117° and ξh=1.99, LGS is 18.9 MHz in the QL mode (m=2) when θ=118° and ξh=2.08, LGN is 17.9 MHz in the QL mode (m=2) when θ=116° and ξh=1.99, GaPO$_4$ is 19.3 MHz in the QL mode (m=2) when θ=135.54° and ξh=2.80. Therefore, an oscillation frequency higher than that of the AT-cut crystal is obtained.

By using these materials to construct the piezoelectric sensor 1, a piezoelectric sensor with high sensitivity can be formed. Similarly, the QS mode also has a piezoelectric crystalline material and a rotation angle θ with an oscillation frequency higher than the AT-cut crystal having the same plate thickness. In addition, LiNbO$_3$ and PZT, etc., have a higher electromechanical coupling factor and a higher energy efficiency when exciting the QL mode or the QS mode than the AT-cut crystal.

Figure 6:
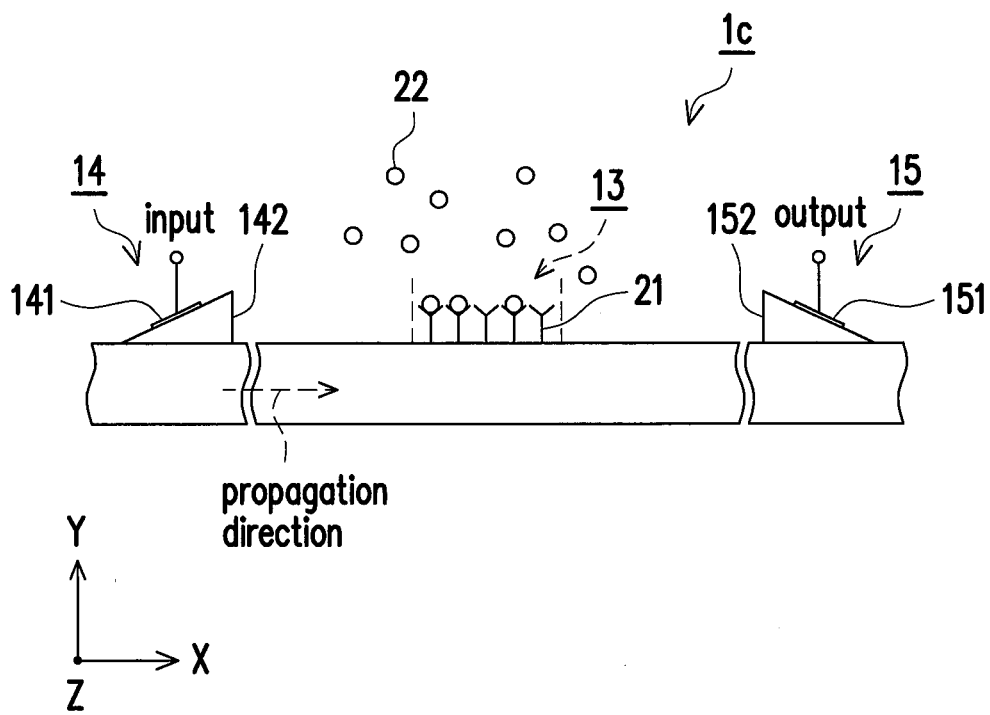
FIG. 6 is a diagram showing an exemplary structure of a sensing sensor having a probe type transducer.

The QL mode and the QS mode are not limited to the case of exciting by using a piezoelectric effect by exciting electrodes (such as the IDT electrodes 11, 12 as shown in FIG. 2-FIG. 5). For example, a sonic wave can be incident into the piezoelectric plate 10 by using a probe type transducer so as to excite these modes. FIG. 6 is an example for the sensing sensor 1c, in which a first transducer 14 on an input side and a second transducer 15 on an output side are located on the principle surface of the piezoelectric plate 10, in a manner that the first transducer 14 and the second transducer 15 are arranged along the propagation direction of the guided wave and opposite to each other to sandwich the detection region. In the figure, 141, 151 are piezoelectric oscillators for converting an inputted and/or outputted electrical signal into a sonic wave, and 142, 152 are wedges for adjusting an incident/exit angle of the sonic wave.

EMBODIMENT

Simulation

A simulation to search excitation conditions of the QL mode and the QS mode is performed for LiNbO$_3$ and PZT (PZT5H), which are the piezoelectric crystalline materials.

Embodiment 1

Using LiNbO$_3$ as the piezoelectric crystalline material, variations of the four roots ($\lambda_1$-$\lambda_4$) of the equation (15) when changing a rotation angle θ around the X-axis of the rotated Y-plate are observed, and the excitation conditions of the QL mode and the QS mode are searched. LiNbO$_3$ belongs to a class 3m of trigonal system, and a three-fold symmetry axis is taken as the Z-axis and the X-axis is taken to be vertical to the Y-Z axis, the mirror plane. A physical property of LiNbO$_3$ is $c_{11}$=2.030×10$^{11}$ [N/m], $c_{66}$=5.5384×10$^{10}$ [N/m], $V_L$=6614.4 [m/s] and ρ=4640 [kg/m$^3$], and it is assumed that $C_{pn}$=1.

Figure 7A:
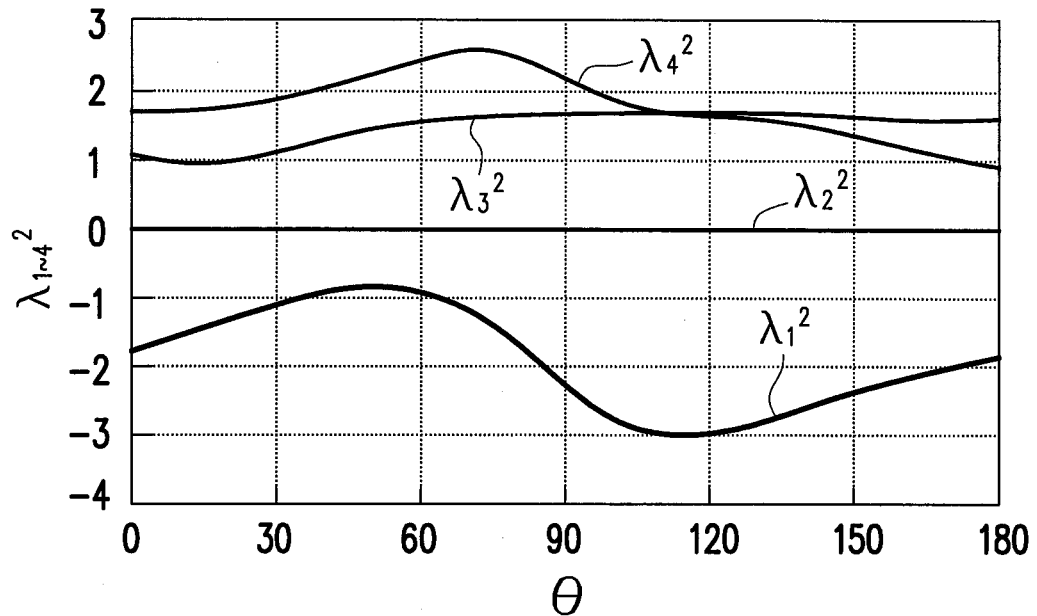
FIGS. 7A and 7B are explanatory graphs showing root loci of equations of motion when changing a rotation angle around the X-axis on a rotated Y-plate of $LiNbO_3$.
Figure 7B:
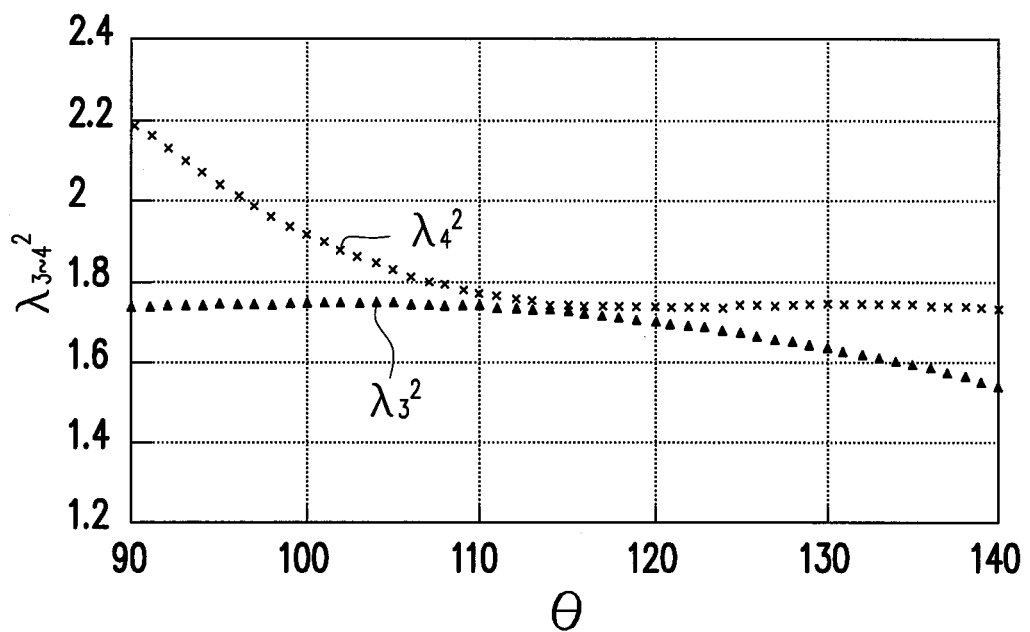

Loci of the roots ($\lambda_1$-$\lambda_4$) of the equation (15) when changing a rotation angle θ of the rotated Y-plate are shown in FIG. 7A and FIG. 7B. FIG. 7A shows squared values of λ, within a range of θ=0-180°, and FIG. 7B is an enlarged view of FIG. 7A and shows a range of θ=90-140° in which there are two adjacent roots.

According to the results shown in FIG. 7A and FIG. 7B, since $\lambda_3$ and $\lambda_4$ are adjacent when the rotation angle θ=114°, it can be expected that the rotation angle is a cut angle which has the multiple root, that is, a cut angle which can excite the QL mode and the QS mode.

Figure 8A:
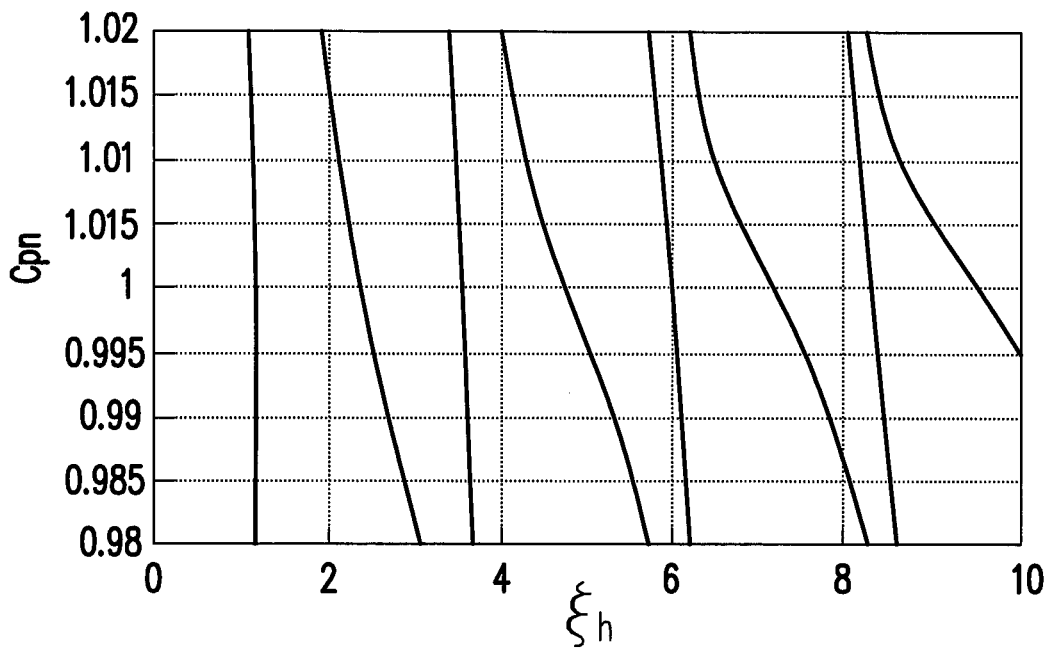
FIGS. 8A and 8B are dispersion curves when the rotation angle of $LiNbO_3$ is 114°.
Figure 8B:
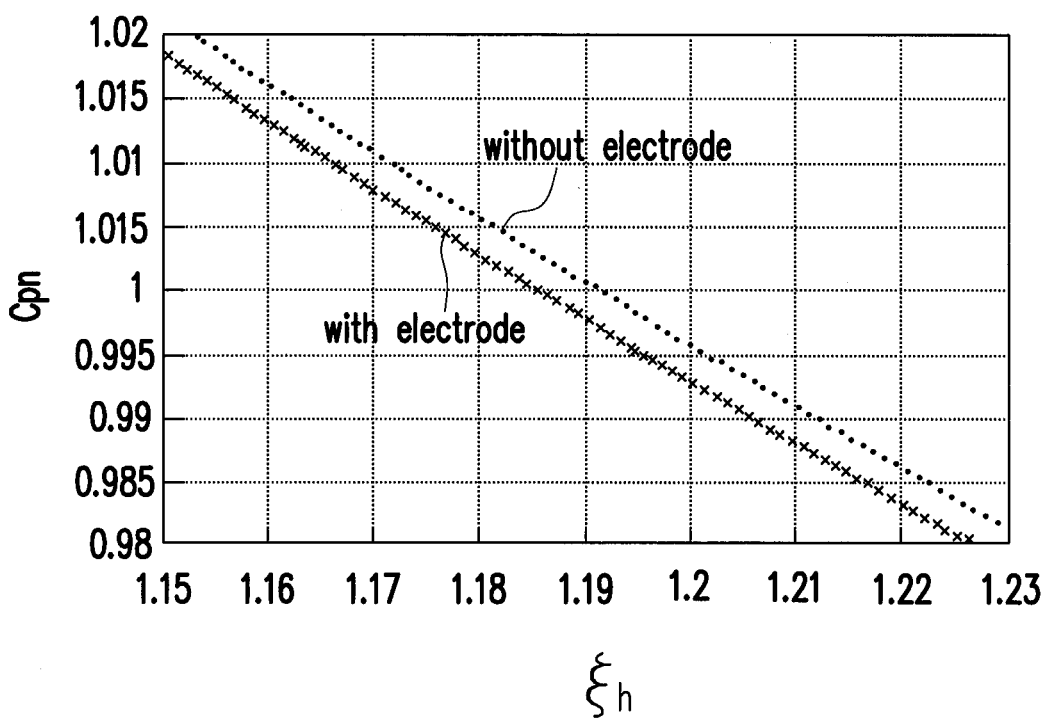

Then, for the rotated Y-plate with θ=114°, dispersion curves in the case that the electrodes are not formed (the equation (13)) and in the case that the electrodes are formed and a top and a bottom electrodes are shorted (the equation (14)) are obtained. These dispersion curves are shown in FIG. 8A and FIG. 8B. In FIG. 8A and FIG. 8B, a horizontal axis shows ξh and a vertical axis shows $C_{pn}$. FIG. 8A is a view showing ξh within a range of 0-10 in wide-angle, and FIG. 8B is an enlarged view of ξh within a range of 1.15-1.23.

Referring to FIG. 7B, when squared values of the multiple roots of $\lambda_3$ and $\lambda_4$ are approximated by 1.74, $\lambda_3$=$\lambda_4$≈1.32 can be obtained, and by calculating equation (18) with m=1, ξh=1.19 can be obtained. According to the enlarged view of FIG. 8B, it is found that the dispersion curves exist in the vicinity of $C_{pn}$=1 when ξh=1.19 so that the guided wave having a frequency corresponding to this $C_{pn}$ can be excited. In addition, although it is not clear in FIG. 8A, according to the enlarged view of FIG. 8B, there is a difference between the dispersion curve with the electrodes and the dispersion curve without the electrodes so that the piezoelectrical excitation is possible.

Based on the results of the above studies, the rotation angle θ=114°, the approximate value of the multiple root λ=1.32 and h=100 [μm], and varying the value of m in the equation (18) with 1, 2, 3, 4, the displacement distributions of the P wave component, the SV wave component and the SH wave component of the guided wave excited in the LiNbO$_3$ piezoelectric plate 10 are calculated in considering piezoelectricity.

Figure 9A:
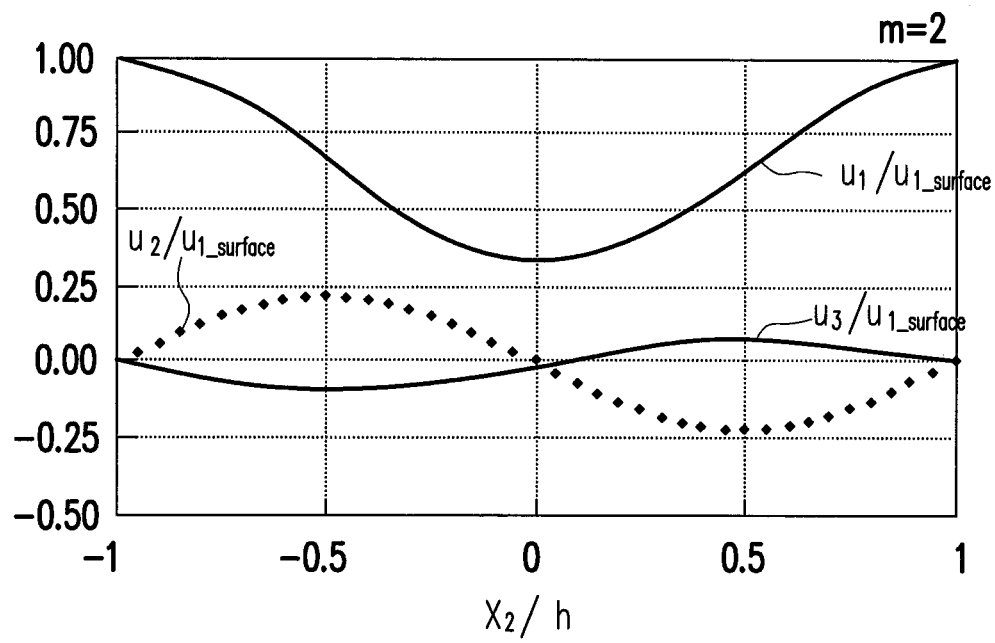
FIGS. 9A and 9B are explanatory graphs showing displacement distributions of the QL mode when changing a value of m on $LiNbO_3$.
Figure 9B:
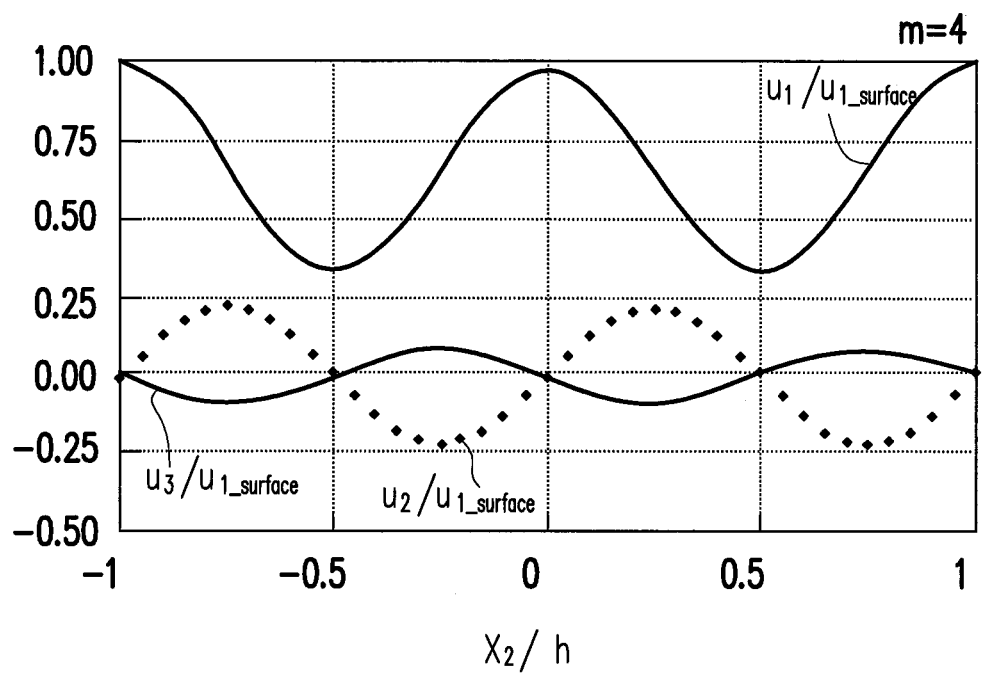

Displacement distributions of each component when m=2 (ξh=2π/(2λ)≈2.39) are shown in FIG. 9A, and displacement distributions of each component when m=4 (ξh=4π/(2λ)≈4.77) are shown in FIG. 9B. The horizontal axis represents a location where a displacement $x_2$ in the Y-axis direction shown in FIG. 1 is normalized by a half plate thickness of the piezoelectric plate 10, and the vertical axis is a the displacement amount in which a displacement of the P wave component ($u_1$), a displacement of the SV wave component ($u_2$) and a displacement of the SH wave component ($u_3$) are normalized by a displacement of the P wave component ($u_{1\text{-}surface}$), on the surface (X-Z plane) of the piezoelectric plate 10.

According to FIG. 9A and FIG. 9B, in both cases, the displacement of the P wave component $u_1$ is the maximum, and the displacement of the SV wave component $u_2$ and the displacement of the SH wave component $u_3$ are approximately zero on the surface of the piezoelectric plate 10. Additionally, the P wave component is larger than the SV wave component and the SH wave component inside the piezoelectric plate 10 as well. Based on these factors, it can be said that the QL mode is excited under the simulation condition in FIG. 9A and FIG. 9B.

For example, when the QL mode is as shown in FIG. 9A, the frequency of the guided wave excited on the piezoelectric plate 10 is f≈2 5.2 MHz, the wave length is Λ≈262.5 μm, and the electrode finger pitch between the IDT electrode 11 and the IDT electrode 12 is d≈65.6 μm.

Figure 11A:
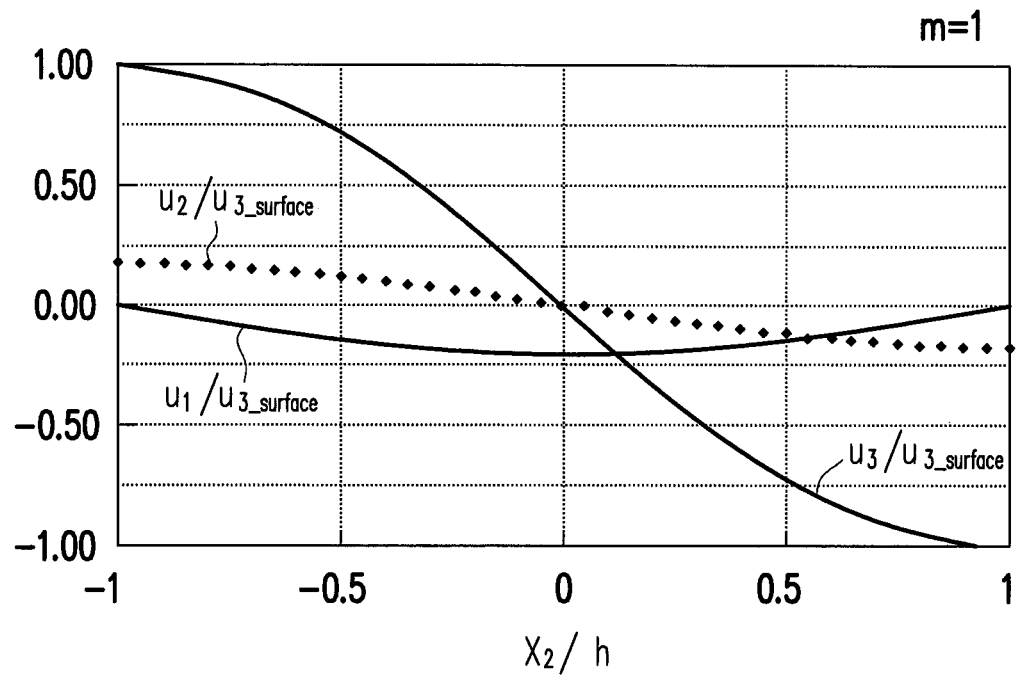
FIGS. 11A and 11B are explanatory graphs showing displacement distributions of the QS mode when changing a value of m in $LiNbO_3$.
Figure 11B:
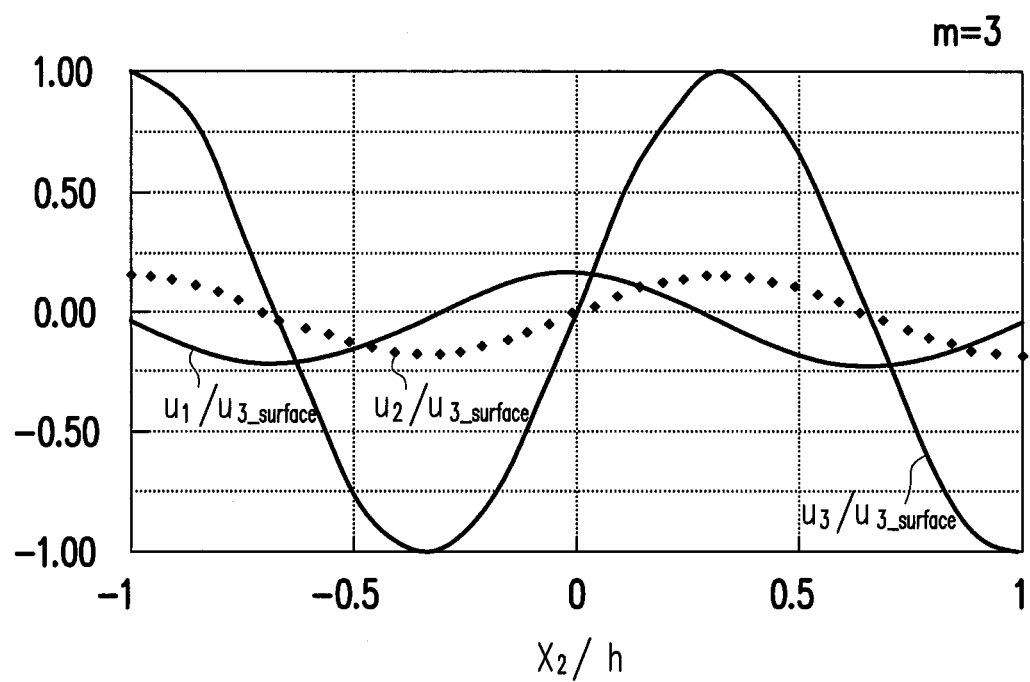

Next, displacement distributions of each component when m=1 (ξh=π/(2λ)≈1.19) are shown in FIG. 11A, and displacement distributions of each component when m=3 (ξh=3π/(2λ)≈3.57) are shown in FIG. 11B. The representation of the horizontal axis is the same as described in FIG. 9, but the vertical axis represents a displacement amount in which the displacement of the P wave component ($u_1$), the displacement of the SV wave component ($u_2$) and the displacement of the SH wave component ($u_3$) are normalized by a displacement of the SH wave component ($u_{3\text{-}surface}$) on the surface of the piezoelectric plate 10.

According to FIG. 11A and FIG. 11B, in both cases, the displacement of the SH wave component $u_3$ is the maximum, and the P wave component $u_1$ is approximately zero on the surface of the piezoelectric plate 10. Additionally, the SH wave component is larger than the P wave component inside the piezoelectric plate 10 as well. Based on these factors, it can be said that the QS mode is excited under the simulation condition in FIG. 11A and FIG. 11B. Besides, either on the surface or inside the piezoelectric plate 10, the SH wave component is larger than the SV wave component.

For example, when the QS mode is as shown in FIG. 11A, the frequency of the guided wave excited on the piezoelectric plate 10 is f≈12.5 MHz, the wave length is Λ≈527.4 μm, and the electrode finger pitch between the IDT electrode 11 and the IDT electrode 12 is d≈132 μm.

According to the above studies, it can be confirmed that the QL mode and the QS mode can be excited on the rotated Y-plate with the rotation angle θ=114° and the solution of the equation (15) is multiple root. However, in some cases, even in a location where the rotation angle θ is shifted from a certain cut direction of $\lambda_3 \approx \lambda_4$, the QL mode or the QS mode can be used.

For example, in a mode that the displacement of the P wave component is the maximum on the surface of the piezoelectric plate 10, when the displacement of the SV wave component or the SH wave component existing on the surface becomes too large to ignore, a longitudinal wave, etc., is induced into a fluid of a measurement object so that problems that an interference of the measurements of an adsorption of the sensing object and a viscosity of the fluid may occur. However, if the displacements of the SV wave component and the SH wave component are, for example, less than 10% of the displacement of the P wave component, the above-mentioned problems can be mostly ignored; therefore, there is no practical problem even if the QL mode is used.

For each of the piezoelectric plate 10 in which the rotation angle θ of the Y-plate of $LiNbO_3$ is changed, displacements of each wave component are calculated, and an absolute value of a difference Δλ between $\lambda_3$ and $\lambda_4$ shown in FIG. 7A and a value of the ratio of the displacement of the SV wave component or the SH wave component to the displacement of the P wave component (below describe as "displacement ratio") are studied.

Figure 10A:
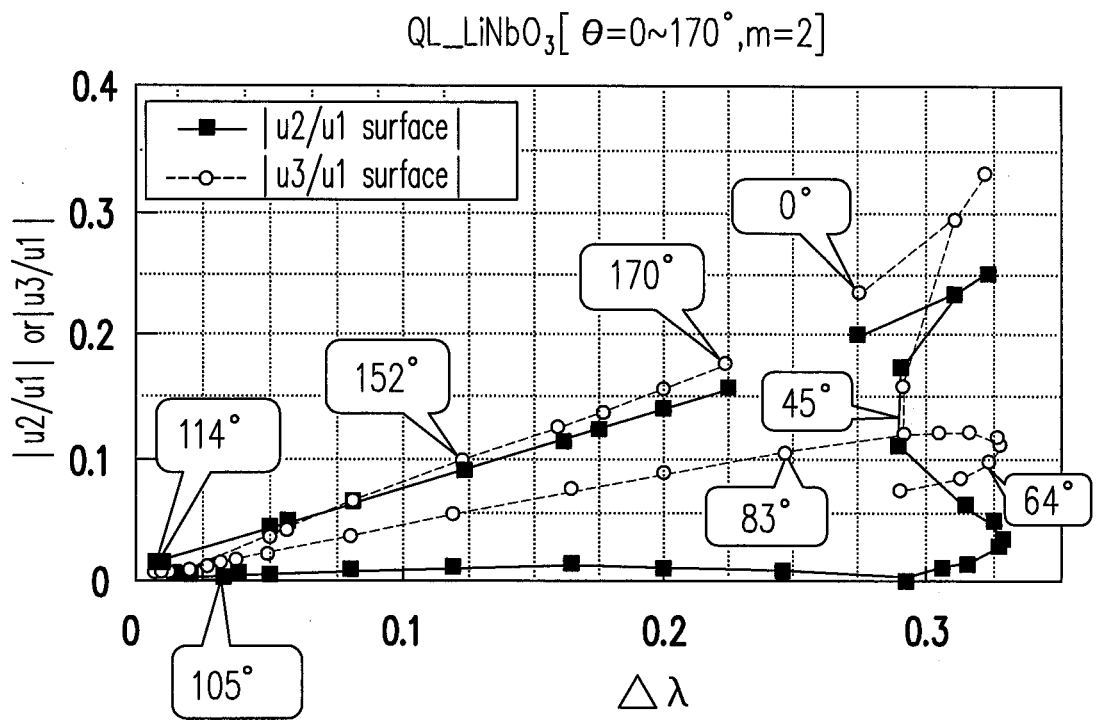
FIGS. 10A and 10B are explanatory graphs showing variations of displacement ratios for each component of the QL mode in $LiNbO_3$ when changing the rotation angle.
Figure 10B:
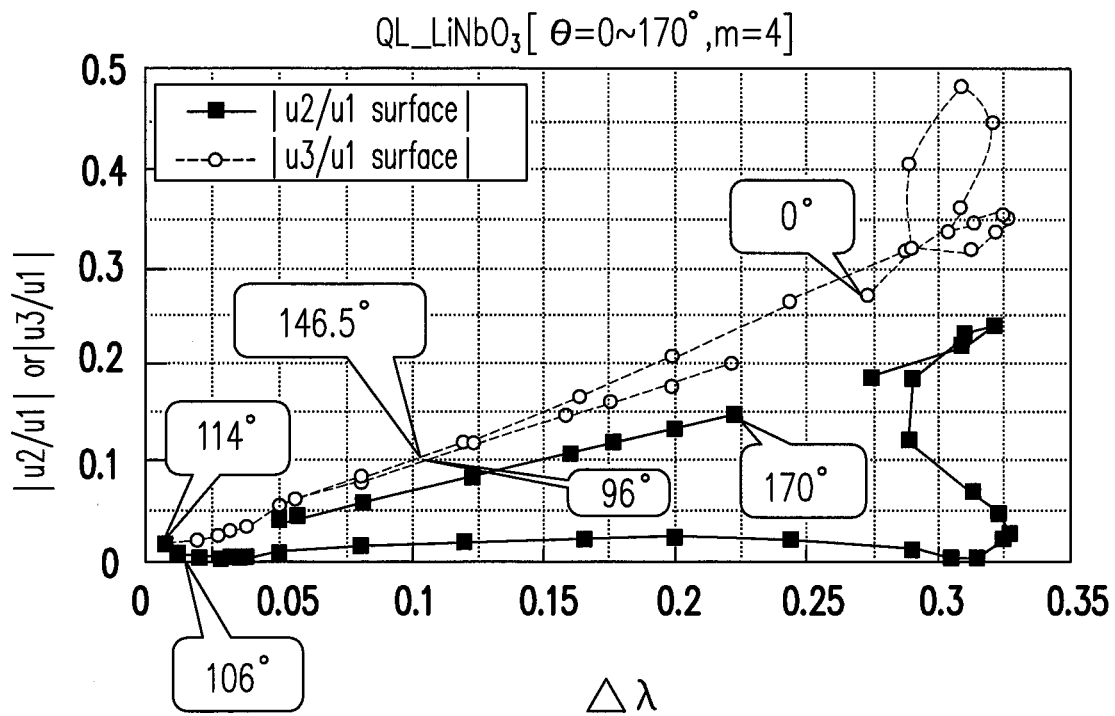

Variations of the displacement ratios when m=2 are shown in FIG. 10A, and variations of the displacement ratios when m=4 are shown in FIG. 10B. In the case of the example for m=2 as shown in FIG. 10A, if within a range of the rotation angle θ with approximately 45°-64°, 83°-152°, the displacement ratio can be reduced to less than 10%. In addition, in the case of the example for m=4 as shown in FIG. 10B, if within a range of the rotation angle θ with approximately 96°-146.5°, the displacement ratio becomes less than 10%.

A similar discussion can be made for the QS mode. But, in $LiNbO_3$, even if it is a theoretical QL mode using the rotation angle θ=114°, the displacement of the SV wave component to the SH wave component becomes over 10%. However, since any practical problems cannot be found even if the displacement ratio is over 10%, a range of the displacement ratio of the P wave component to the SH wave component less than 10%, or a range of the displacement ratio of the SH wave component to the SV wave component less than 20% can be set for the QS mode.

Figure 12A:
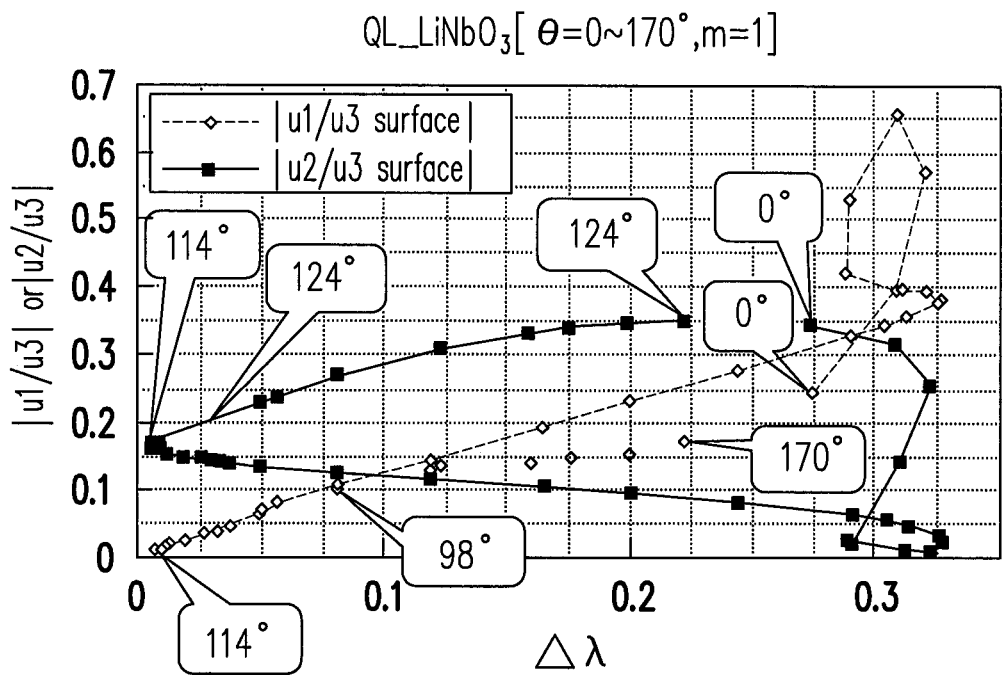
FIGS. 12A and 12B are explanatory graphs showing variations of displacement ratios for each component of the QS mode in $LiNbO_3$ when changing the rotation angle.
Figure 12B:
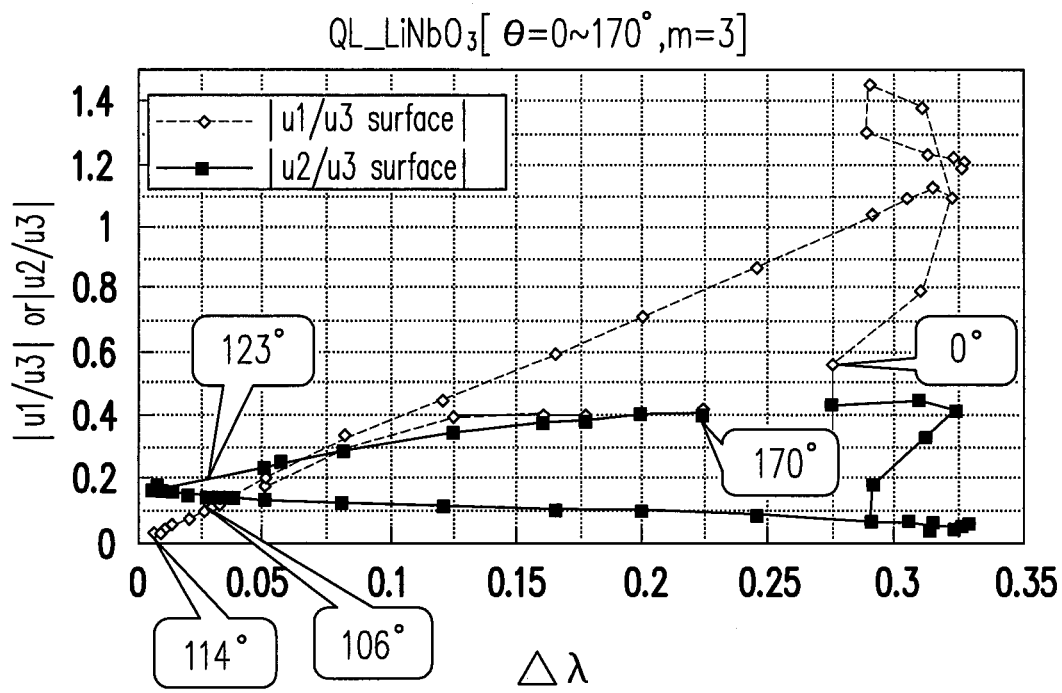

Variations of the displacement ratios when m=1 are shown in FIG. 12A, and variations of the displacement ratios when m=3 are shown in FIG. 12B. In the case of the example for m=1 as shown in FIG. 12A, if within a range that the simulation was performed, the displacement ratio of the P wave component can be reduced to less than 10% and the displacement ratio of the SV wave component can be reduced to less than 20% in a range of the rotation angle θ with approximately 98°-124°. In addition, in case of the example for m=3 as shown in FIG. 12B, within a range that the simulation was performed, if within a range of the rotation angle θ with approximately 106°-123°, the displacement ratio of the P wave component becomes less than 10% and the displacement ratio of the SV wave component becomes less than 20%.

Embodiment 2

Using PZT (PZT5H) as the piezoelectric crystalline material, variations of the four roots ($\lambda_1$-$\lambda_4$) of the equation (15) when changing a rotation angle θ around the X-axis of the rotated Y-plate are observed, and the excitation conditions of the QL mode and the QS mode are studied. For PZT after a poling process is performed, when a direction of performing the poling process is assumed as the Z-axis, any axis vertical to the Z-axis is the X-axis and an axis vertical to the X-axis is the Y-axis (of course, the Y-axis is also vertical to the Z-axis). Even though being rotated around the Z-axis, the character of PZT does not change, i.e., the so-called transversely isotorropic. The calculation can be made as crystal system 6v, however, the Z-axis is not a six-fold symmetry and has higher order symmetry. A physical property of PZT is $c_{11}=1.272 \times 10^{11}$ [N/m], $c_{66}=2.303 \times 10^{10}$ [N/m], $V_L=4118.3$ [m/s], $\rho=7500$ [kg/m$^3$], and $C_{pn}=1$ is assumed.

Figure 13A:
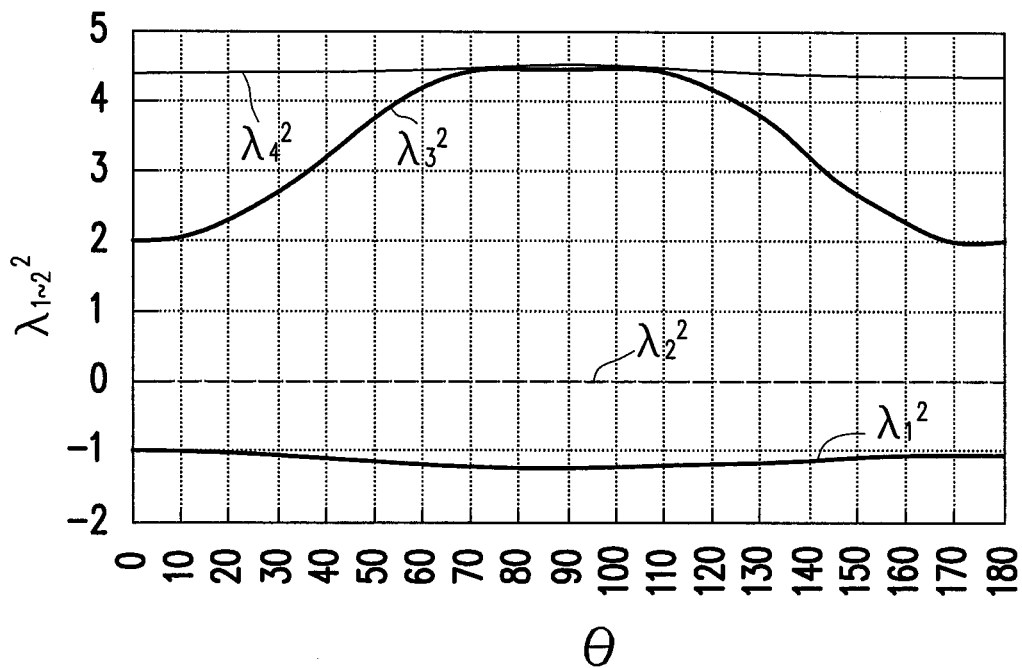
FIGS. 13A and 13B are explanatory graphs showing root loci of equations of motion when changing a rotation angle around the X-axis on a rotated Y-plate of PZT5H.
Figure 13B:
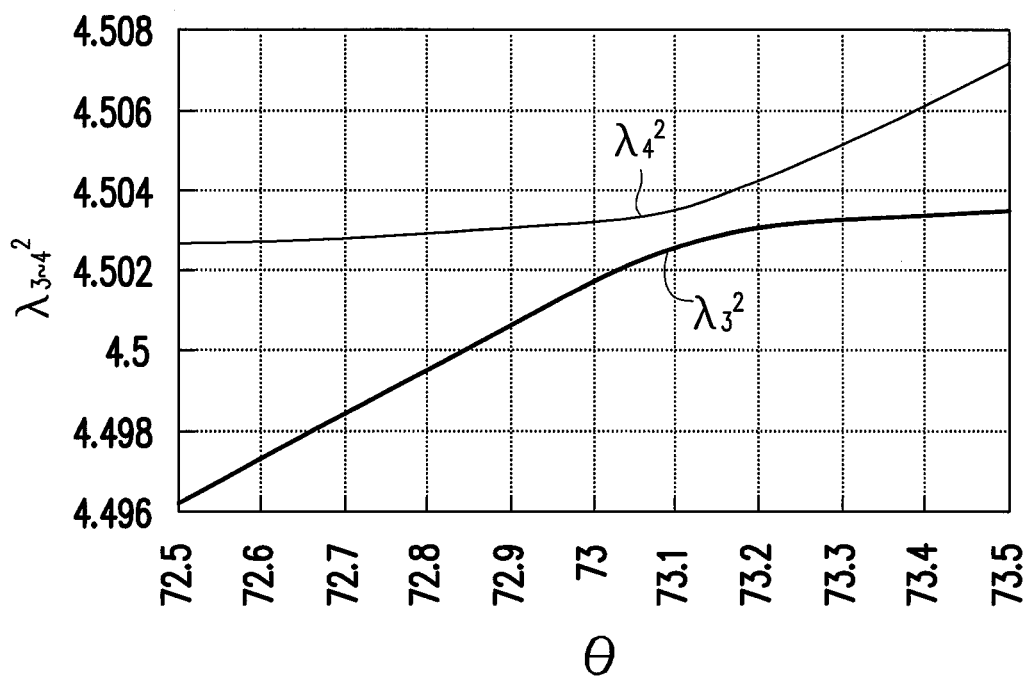

Loci of the roots ($\lambda_1$-$\lambda_4$) of the equation (15) when changing a rotation angle θ around the X-axis of the rotated Y-plate are shown in FIG. 13A and FIG. 13B. FIG. 13A shows squared values of X, within a range of θ=0-180°, and FIG. 13B is an enlarged view of FIG. 13A and shows around θ=73.12° which has two adjacent roots.

According to the results shown in FIG. 13A and FIG. 13B, since $\lambda_3$ and $\lambda_4$ are close to each other in the two cases of the rotation angles θ=73.12° and θ=106.88°, it can be expected that the rotation angle is a cut angle which has multiple root, which is a cut angle that can excite the QL mode and the QS mode.

Figure 14A:
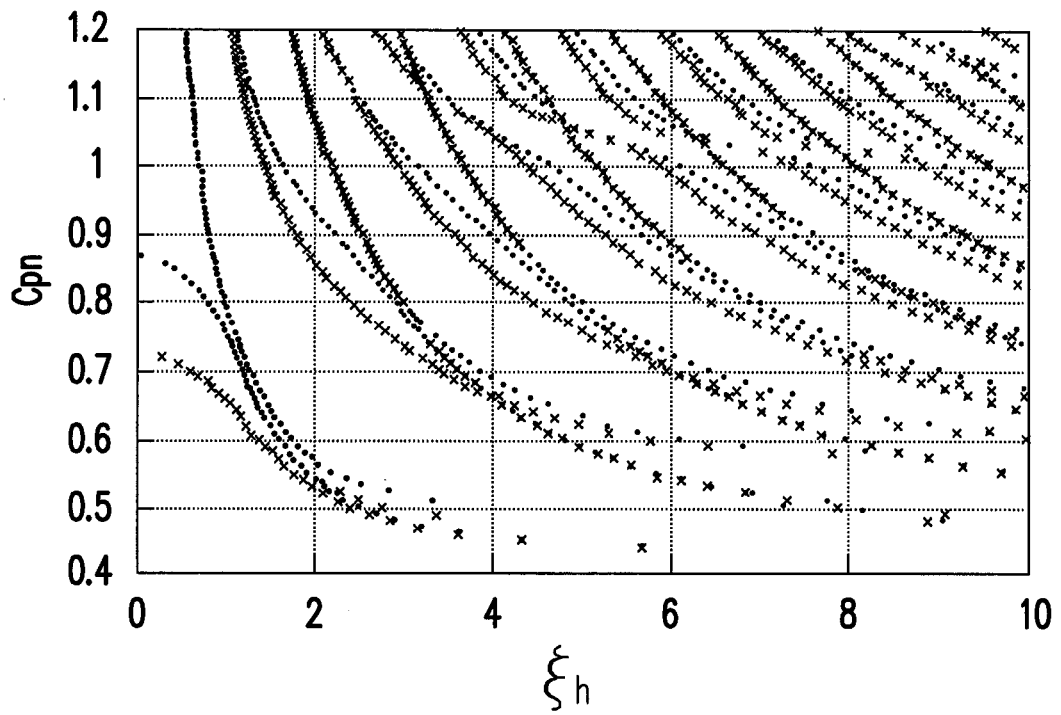
FIGS. 14A and 14B are dispersion curves when the rotation angle of PZT5H is 73.12°.
Figure 14B:
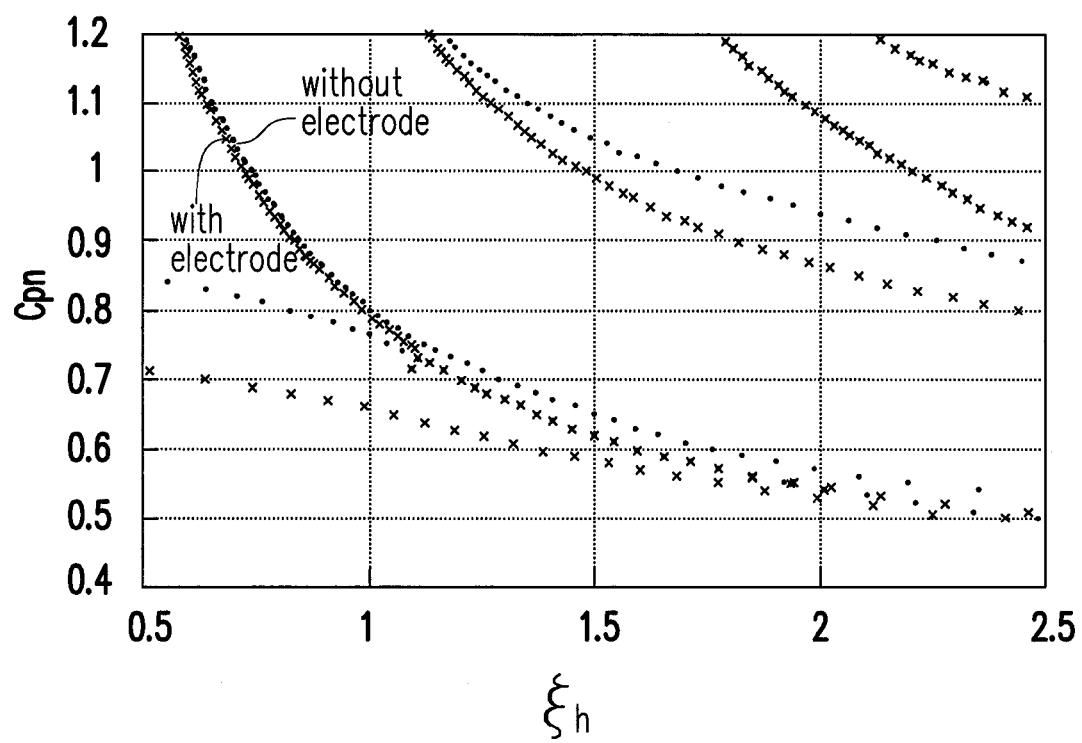

Then, for the rotated Y-plate with θ=73.12°, dispersion curves in the case that the electrodes are not formed (equation (13)), and in the case that the electrodes are formed and a top and a bottom electrodes are shorted (the equation (14)) are obtained. These dispersion curves are shown in FIG. 14A and FIG. 14B. A horizontal axis and a vertical axis are the same as described in FIG. 8. FIG. 14A is a view showing ξh within a range of 0-10 in wide-angle, and FIG. 14B is an enlarged view of ξh within a range of 0.5-2.5.

Referring to FIG. 14B, when squared values of the multiple roots of $\lambda_3$ and $\lambda_4$ are approximated by 4.503, $\lambda_3=\lambda_4\approx2.18$ can be obtained, and by calculating the equation (18) with m=1, ξh=0.72 can be obtained. According to the enlarged view of FIG. 14B, it is found that the dispersion curves exist in the vicinity of $C_{pn}=1$ when ξh=0.72, so that the guided wave having a frequency corresponding to this $C_{pn}$ can be excited. In addition, although it is not clear in FIG. 14A, according to the enlarged view of FIG. 14B, there is a difference between the dispersion curve with the electrodes and the dispersion curve without the electrodes so that piezoelectrical excitation is possible.

Based on the results of the above studies, by assuming that the rotation angle θ=73.12°, the approximate value of the multiple root λ=2.18 and h=100 [μm] and varying the value of m in the equation (18) with 1, 2, 3, 4, displacement distributions of the P wave component, the SV wave component and the SH wave component of the guided wave excited in the PZT piezoelectric plate 10 are calculated in considering piezoelectricity.

Figure 15A:
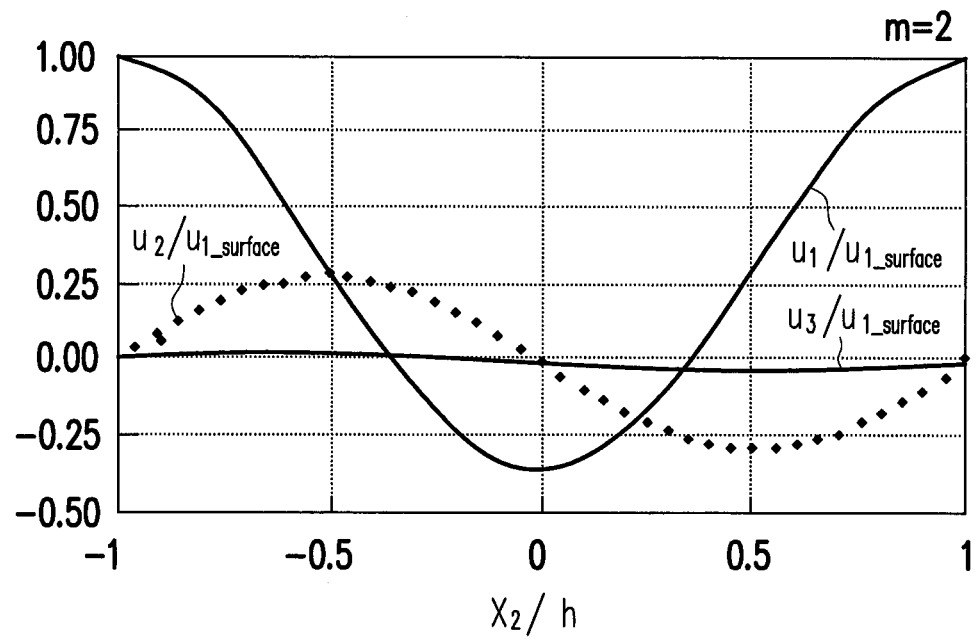
FIGS. 15A and 15B are explanatory graphs showing displacement distributions of the QL mode when changing a value of m on PZT5H.
Figure 15B:
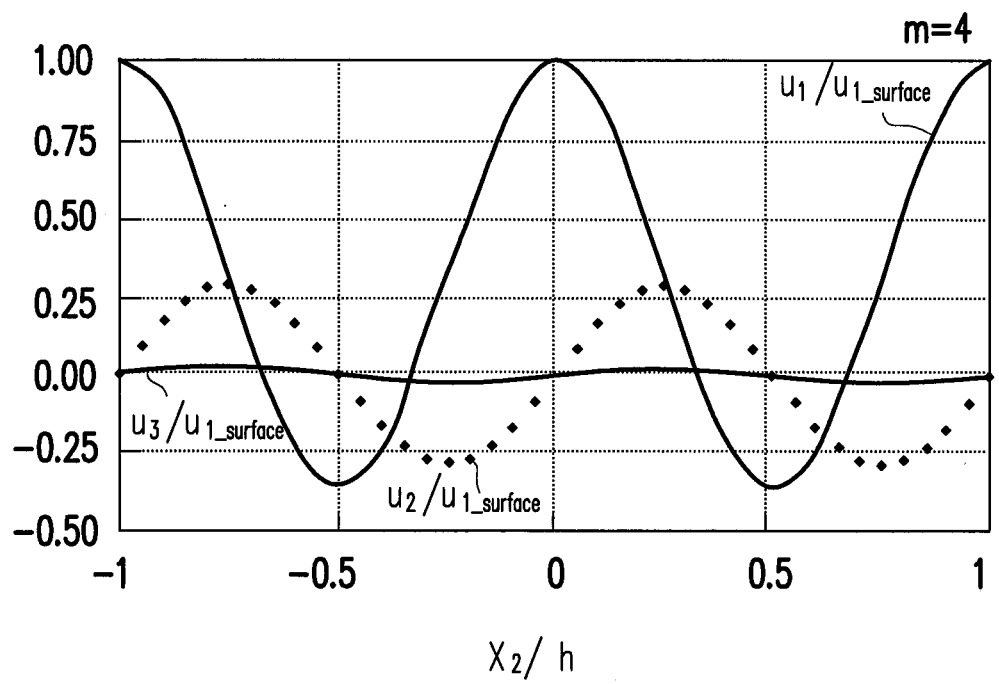

Displacement distributions of each component when m=2 (ξh=2π/(2λ)≈1.48) are shown in FIG. 15A, and displacement distributions of each component when m=4 (ξh=4π/(2λ) ≈2.96) are shown in FIG. 15B. Definitions of the horizontal axis and the vertical axis are the same as described in FIG. 9.

According to FIG. 15A and FIG. 15B, in both cases, the displacement of the P wave component $u_1$ is the maximum, and the displacement of the SV wave component $u_2$ and the displacement of the SH wave component $u_3$ are approximately zero on the surface of the piezoelectric plate 10. Additionally, the P wave component is larger than the SV wave component and the SH wave component inside the piezoelectric plate 10. Based on these factors, it can be said that the QL mode is excited under the simulation condition in FIG. 15A and FIG. 15B.

For example, when the QL mode is as shown in FIG. 15A, the frequency of the guided wave excited on the piezoelectric plate 10 is f≈9.7 MHz, the wave length is Λ≈424.5 μm, and the electrode finger pitch between the IDT electrode 11 and the IDT electrode 12 is d≈106 μm.

Figure 17A:
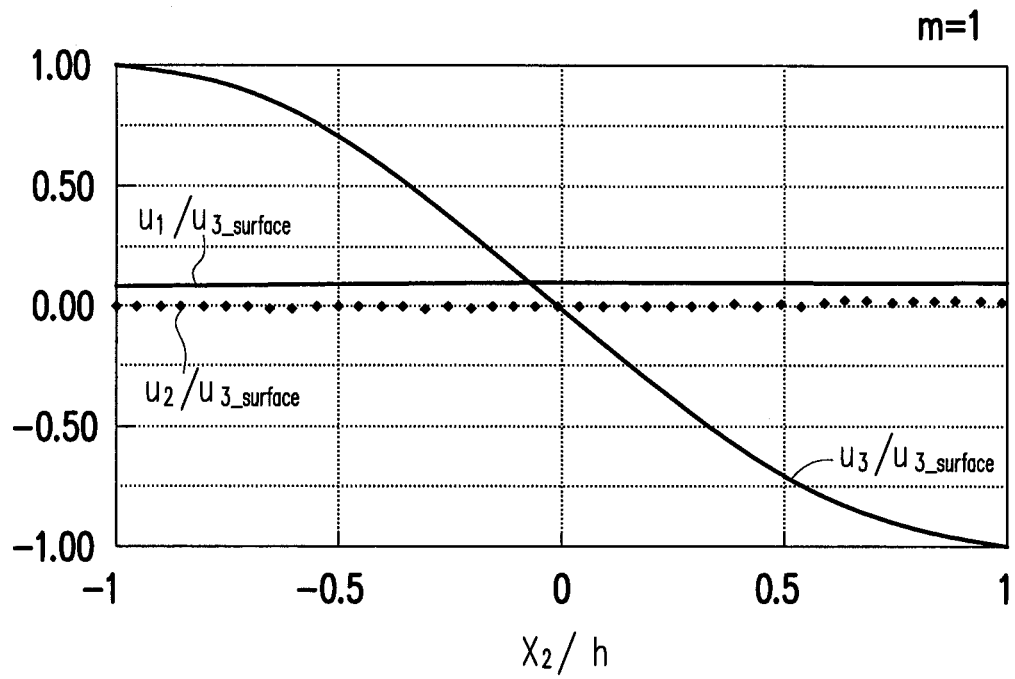
FIGS. 17A and 17B are explanatory graphs showing displacement distributions of the QS mode when changing a value of m in PZT5H.
Figure 17B:
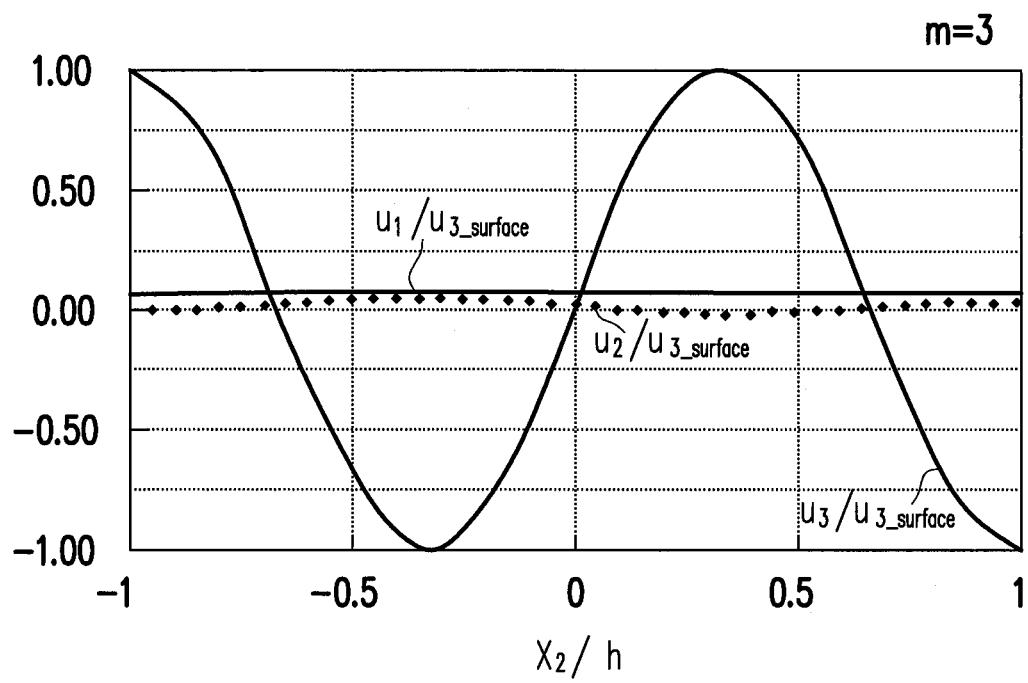

Next, displacement distributions of each component when m=1 (ξh=π/(2λ)≈0.72) are shown in FIG. 17A, and displacement distributions of each component when m=3 (ξh=3π/(2λ)≈2.21) are shown in FIG. 17B. Definitions of the horizontal axis and the vertical axis are the same as described in FIG. 11.

According to FIG. 17A and FIG. 17B, in both cases, the displacement of the SH wave component $u_3$ is the maximum, and the P wave component $u_1$ is approximately zero on the surface of the piezoelectric plate 10. Additionally, the SH wave component is larger than the P wave component inside the piezoelectric plate 10. Based on these factors, it can be said that the QS mode is excited under the simulation condition in FIG. 17A and FIG. 17B. Besides, either on the surface or inside the piezoelectric plate 10, the SH wave component is larger than the SV wave component.

For example, when the QS mode is as shown in FIG. 17A, the frequency of the guided wave excited on the piezoelectric plate 10 is f≈4.7 MHz, the wave length is Λ≈872.7 μm, and the electrode finger pitch between the IDT electrode 11 and the IDT electrode 12 is d≈218 μm.

From the above studies, it can be confirmed that the QL mode and the QS mode can be excited on the rotated Y-plate with the rotation angle θ=73.12° where the solution of the equation (15) becomes multiple root. In addition, it can be confirmed that the same result can be obtained when θ=106.88° as well. Below, similar to the discussion in a case of LiNbO$_3$, a range which practically can be used as the QL mode or the QS mode even in a location where the rotation angle θ is shifted from a certain cut direction of $\lambda_3\approx\lambda_4$ is studied.

Figure 16A:
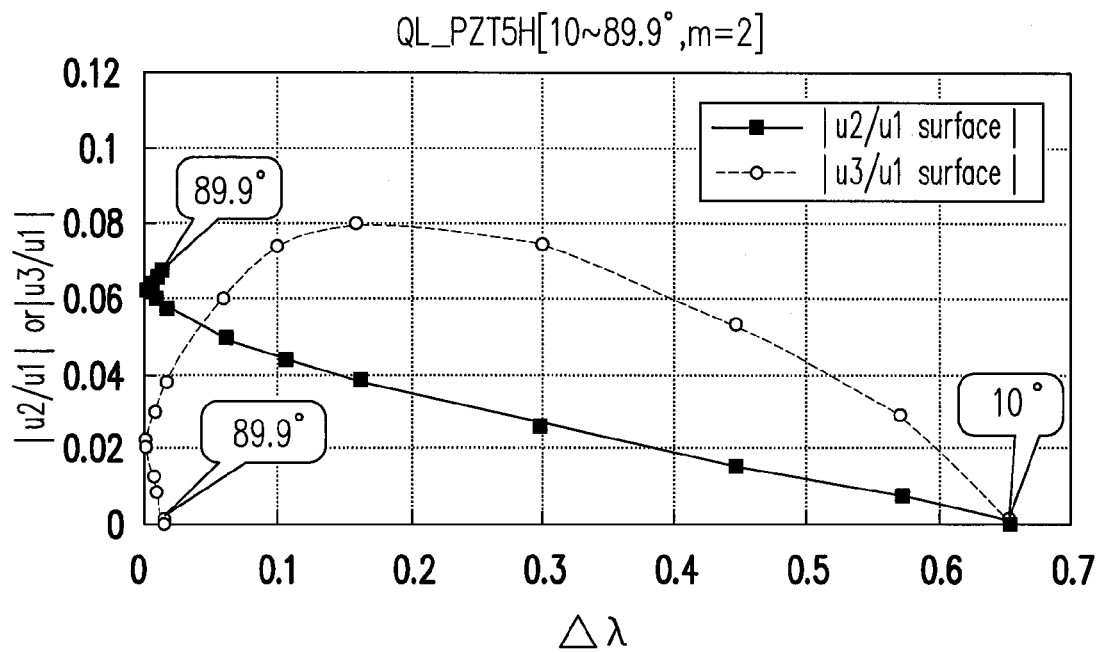
FIGS. 16A and 16B are explanatory graphs showing variations of displacement ratios for each component of the QL mode in PZT5H when changing the rotation angle.
Figure 16B:
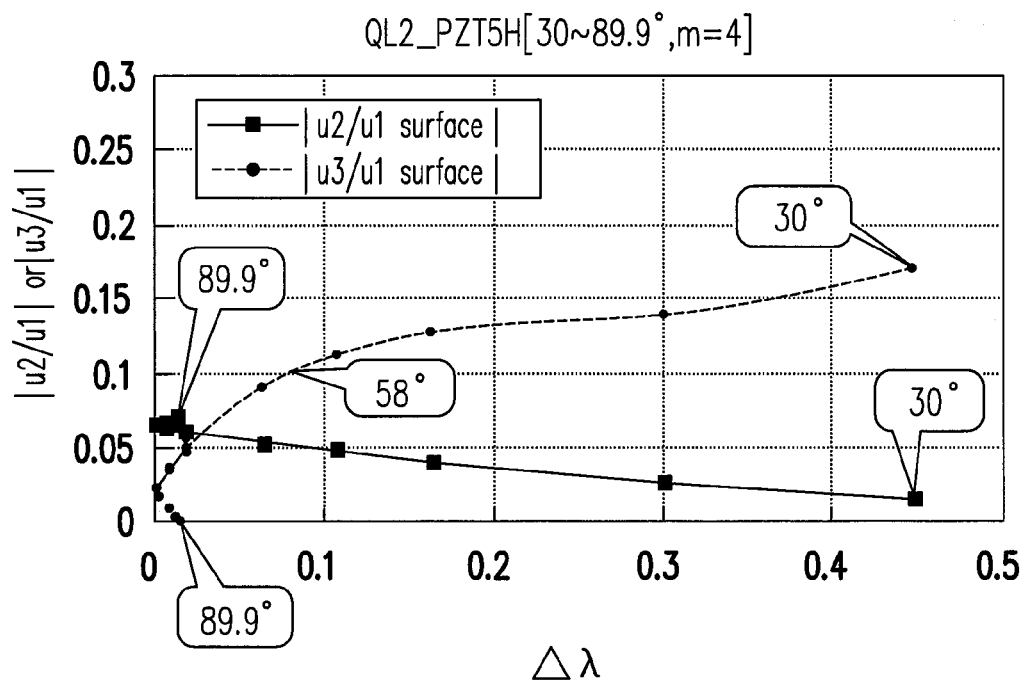

Variations of the displacement ratios when m=2 are shown in FIG. 16A, and variations of the displacement ratios when m=4 are shown in FIG. 16B. Displacement ratios in a range of 10°-90° (89.9°) are shown in FIG. 16A; however, as it is clear from the loci of the roots ($\lambda_1$-$\lambda_4$) in FIG. 13A, the displacement ratios are mirror symmetric with θ=90° as a boundary within a range of 90°-170°. Therefore, in the case of the example for m=2 in FIG. 16A, if the simulation was performed within a range of the rotation angle θ, and a range of approximately 10°-170° which is mirror symmetric with θ=90° as a boundary, the displacement ratios can be reduced to less than 10%. In addition, in the case of the example for m=4 in FIG. 16B, within a range that the simulation was performed, the displacement ratio becomes less than 10% range of the rotation angle θ, which is approximately 58°-90° (89.9°). Therefore, when a range which is mirror symmetric about θ=90° is added, the displacements of the SH wave component and the SH wave component become, for example, less than 10% of the displacements of the P wave component, which is in a range of 58°-122°, so that there is no practical problem even if it is used as the QL mode.

Figure 18A:
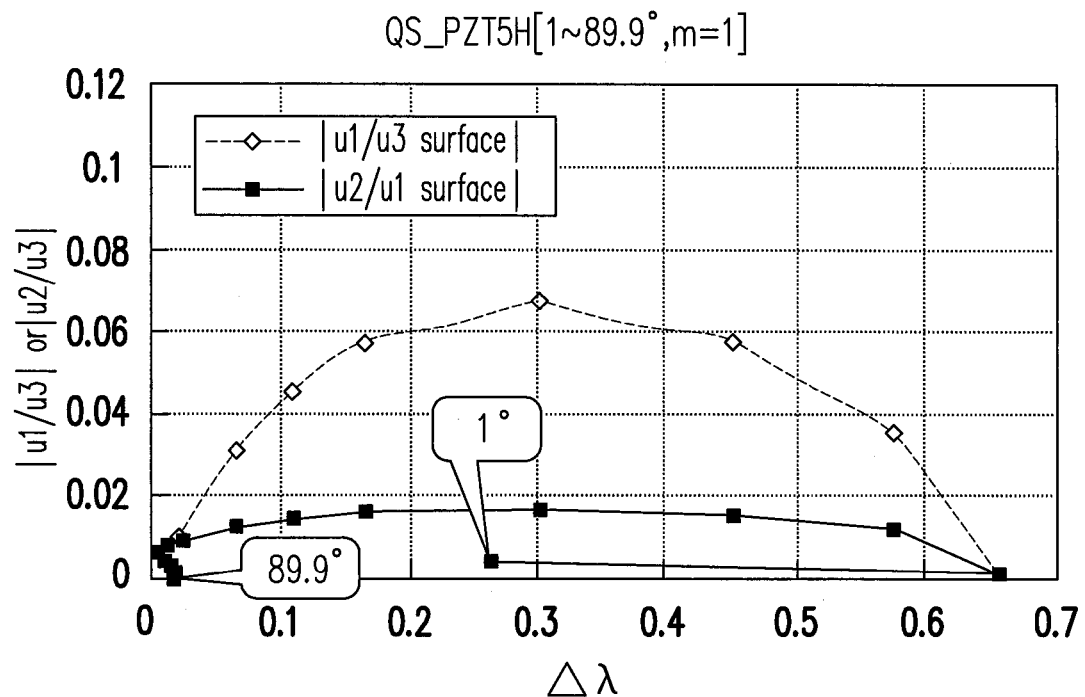
FIGS. 18A and 18B are explanatory graphs showing variations of displacement ratios for each component of the QS mode in PZT5H when changing the rotation angle.
Figure 18B:
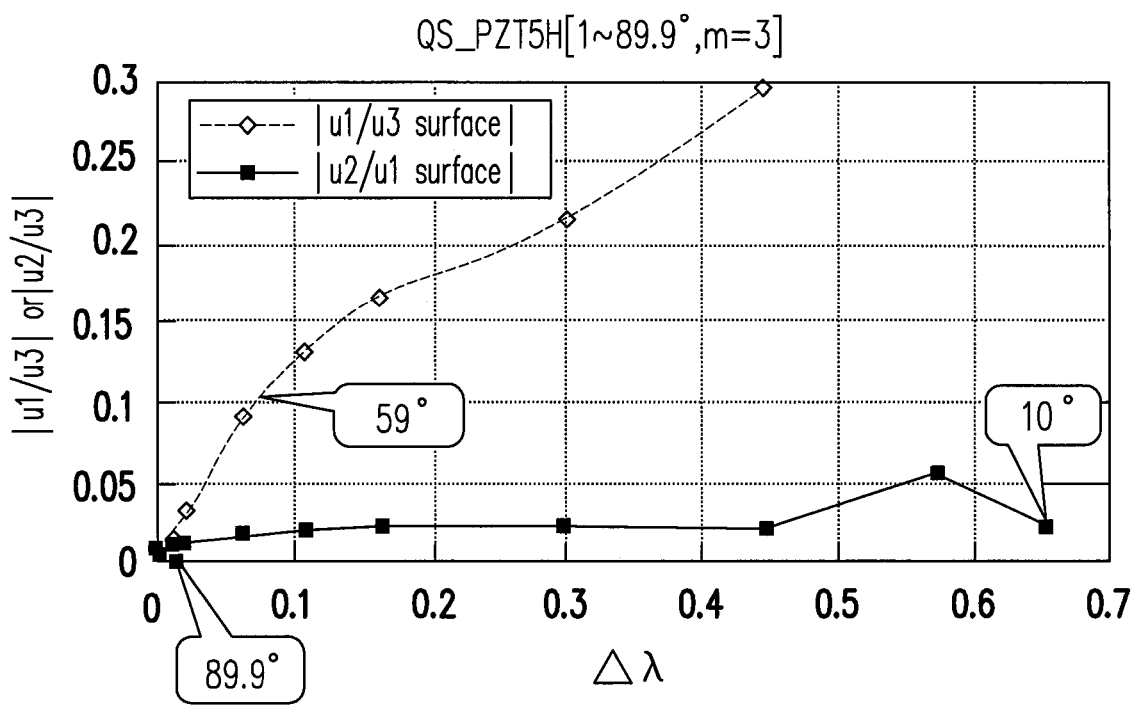

Next, a similar study is conducted for the QS mode of PZT. Variations of the displacement ratios when m=1 are shown in FIG. 18A, and variations of the displacement ratios when m=3 are shown in FIG. 18B. In the case of the example for m=1 in FIG. 18A, if within a range that the simulation was performed and a range which is mirror symmetric with θ=90° as a boundary, the displacement ratios of the P wave and the SV wave can be reduced to less than 10% in a range of the rotation angle θ, which is approximately 0°-180°. In addition, in case of the example for m=3 in FIG. 16B, within a range that the simulation was performed and a range which is mirror symmetric with θ=90° as a boundary, the displacement ratios of the P wave and the SV wave become less than 10% if in a range of the rotation angle θ, which is approximately 59°-121°.

Embodiment 3

Using LTGA as the piezoelectric crystalline material, variations of the four roots ($\lambda_1$-$\lambda_4$) of the equation (15) when changing a rotation angle θ around the X-axis of the rotated Y-plate are observed. LTGA belongs to the trigonal system with point group 32, and a three-fold symmetry axis is taken as the Z-axis, a two-fold symmetry axis is taken as the X-axis and an axis vertical to these axis is taken as the Y-axis. The physical property of LTGA, in which $c_{11}=1.888\times10^{11}$ [N/m], $c_{66}=3.8517\times10^{10}$ [N/m], $V_L=5559.3$ [m/s], ρ=6108.8 [kg/m$^3$], and $C_{pn}=1$, is assumed.

Figure 19:
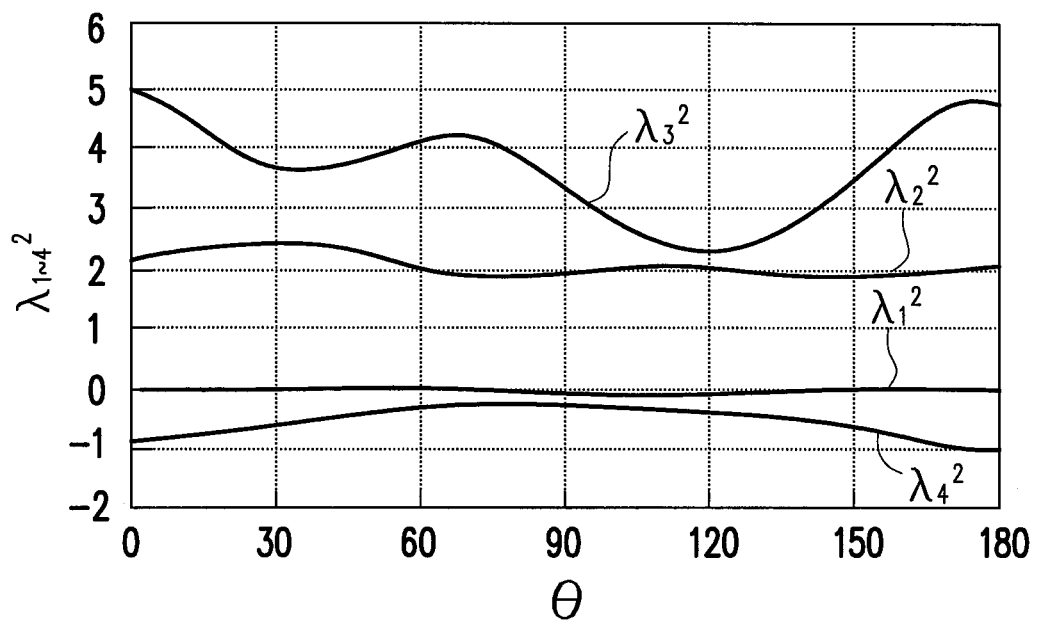
FIG. 19 is an explanatory graph showing root loci of equations of motion when changing a rotation angle around the X-axis on a rotated Y-plate of LTGA.

Loci of the roots ($\lambda_1$-$\lambda_4$) of the equation (15) when changing a rotation angle θ of the rotated Y-plate are shown in FIG. 19. FIG. 19 shows squared values of λ in a range of θ=0-180°. According to the results shown in FIG. 19, although two roots of $\lambda_3$ and $\lambda_4$ are adjacent when the rotation angle θ=116°, the difference was much larger than those of LiNbO$_3$ and PZT; therefore, the two roots cannot be considered as multiple root. However, the obtained dispersion curves (not shown) in the rotation angle exist in the vicinity of $C_{pn}=1$ when ξh=1.06, 2.02; hence, the guided wave with a frequency corresponding to this $C_{pn}$ can be excited.

Then, by assuming the rotation angle θ=116°, h=100 [μm], ξh=2.02 and m in equation (18) is 2, displacement distributions of the P wave component, the SV wave component and the SH wave component of the guided wave excited in the LTGA piezoelectric plate 10 are calculated in considering piezoelectricity. As a result, in a lower order (m=2 in this example), the displacement of the P wave component $u_1$ becomes the maximum while the displacement of the SV wave component $u_2$ and the displacement of the SH wave component $u_3$ become approximately zero on the surface of the piezoelectric plate 10. Inside the piezoelectric plate 10 as well, the QL mode, in which the P wave component is larger than the SV wave component and the SH wave component, was confirmed (not shown). Furthermore, when m=2, the frequency of the guided wave excited on the piezoelectric plate 10 is f≈17.8 MHz, the wave length is Λ≈311.0 μm, and the electrode finger pitch between the IDT electrode 11 and the IDT electrode 12 is d≈77.8 μm. Besides, by performing a reverse calculation for the approximate values of the multiple roots of $\lambda_2$, $\lambda_3$ from ξh=2.02 and performing a high-order calculation with m=4, 6 (ξh=4.04, 6.07 respectively), the displacement of the SH wave component $u_3$ on the surface of the piezoelectric plate 10 becomes larger and the character for the QL mode becomes smaller.

Moreover, in the above-mentioned rotation angle and the half plate thickness h, by assuming ξh=1.06 and m=1 in equation (18), the displacement distributions of the P wave component, the SV wave component and the SH wave component of the guided wave excited in the LTGA piezoelectric plate 10 are calculated in considerating piezoelectricity. As a result, in a lower order (m=1 in this example), the displacement of the SH wave component u3 becomes the maximum, while the displacement of the P wave component u1 and the displacement of the SV wave component u2 becomes approximately zero on the surface of the piezoelectric plate 10. Inside the piezoelectric plate 10, the QS mode, in which the SH wave component is larger than the P wave component and the SV wave component, is confirmed (not shown). Furthermore, when m=1, the frequency of the guided wave excited on the piezoelectric plate 10 is f≈9.4 MHz, the wave length is Λ≈594.4 μm, and the electrode finger pitch between the IDT electrodes 11 and 12 is d≈148.6 μm. Besides, by performing a reverse calculation for the approximate values of the multiple roots of $\lambda_2$, $\lambda_3$ from ξh=1.06 and performing a high-order calculation with m=3, 5 (ξh=3.17, 5.28 respectively), the displacement of the P wave component $u_1$ on the surface of the piezoelectric plate 10 becomes larger and the character for the QS mode becomes smaller.

Embodiment 4

Using LGT as the piezoelectric crystalline material, variations of the four roots ($\lambda_1$-$\lambda_4$) of equation (15), when a rotation angle θ around the X-axis of the rotated Y-plate changes, are observed. Ways to define the X-axis, Y-axis and the X-axis are the same as those described in [Embodiment 3]. The physical property of LGT, in which $c_{11}$=1.885×10$^{11}$ [N/m], $c_{66}$=4.032×10$^{10}$ [N/m], $V_L$=5536.4 [m/s], ρ=6150.4 [kg/m³], and $C_{pn}$=1, is assumed. Herein, the physical property of LGT is based on IEEE-176-1949 (R1971) "Standard on Piezoelectricity".

Figure 20:
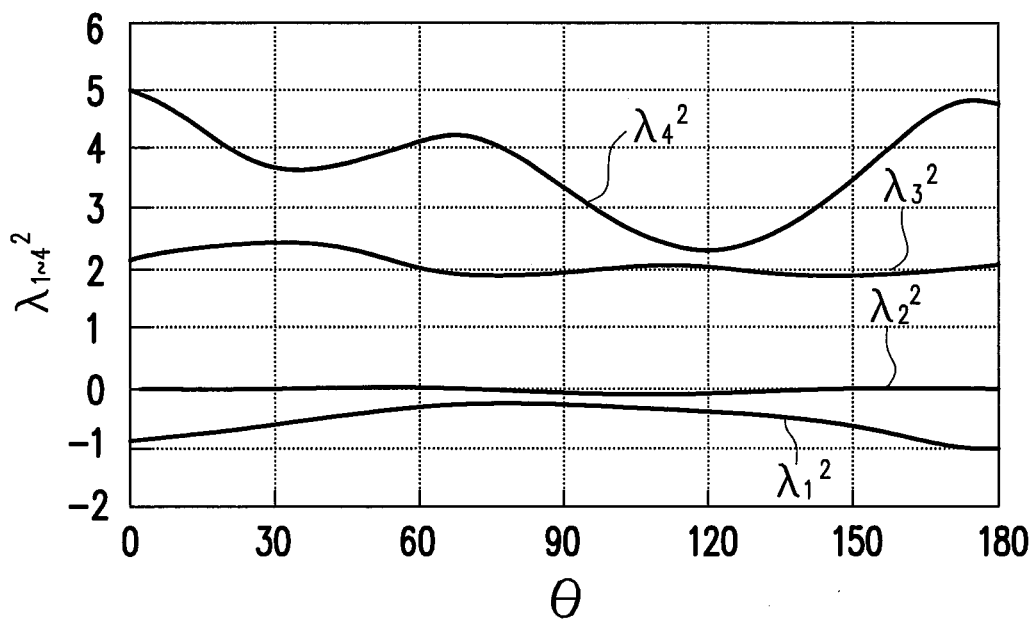
FIG. 20 is an explanatory graph showing root loci of equations of motion when changing a rotation angle around the X-axis on a rotated Y-plate of LGT.

Loci of the roots ($\lambda_1$-$\lambda_4$) of the equation (15), when a rotation angle θ of the rotated Y-plate changes, are shown in FIG. 20. FIG. 20 shows the squared values of λ in a range of θ=0-180°. According to the results as shown in FIG. 20, although two roots of $\lambda_3$ and $\lambda_4$ are adjacent when the rotation angle θ=117°, the difference is much larger than those of LiNbO$_3$ and PZT; therefore, the two roots cannot be considered as multiple root. However, after dispersion curves (not shown) in the rotation angle are obtained, it is found that the dispersion curves exist in the vicinity of $C_{pn}$=1 when ξh=1.05, 1.99, so that the guided wave with a frequency corresponding to this $C_{pn}$ can be excited.

Then, by assuming the rotation angle θ=117°, h=100 [μm], ξh=1.99 and m=2 in the equation (18), the displacement distributions of the P wave component, the SV wave component and the SH wave component of the guided wave excited in the LGT piezoelectric plate 10 are calculated in considering piezoelectricity. As a result, in a lower order (m=2 in this example), the displacement of the P wave component $u_1$ becomes the maximum, while the displacement of the SV wave component $u_2$ and the displacement of the SH wave component $u_3$ become approximately zero on the surface of the piezoelectric plate 10. Inside the piezoelectric plate 10, the QL mode, in which the P wave component is larger than the SV wave component and the SH wave component, is confirmed (not shown). Furthermore, when m=2, the frequency of the guided wave excited on the piezoelectric plate 10 is f≈17.5 MHz, the wave length is Λ≈316.3 μm, and the electrode finger pitch between the IDT electrode 11 and the IDT electrode 12 is d≈79.1 μm. Besides, by performing a reverse calculation for the approximate values of the multiple roots of $\lambda_3$, $\lambda_4$ from ξh=1.99 and performing a high-order calculation with m=4, 6 (ξh=3.98, 5.97 respectively), the displacement of the SH wave component $u_3$ on the surface of the piezoelectric plate 10 becomes larger and the character for the QL mode becomes smaller.

Moreover, in the above-mentioned rotation angle and the half plate thickness h, by assuming ξh=1.05 and m=1 in equation (18), the displacement distributions of the P wave component, the SV wave component and the SH wave component of the guided wave excited in the LGT piezoelectric plate 10 are calculated in considering piezoelectricity. As a result, in a lower order (m=1 in this example), the displacement of the SH wave component $u_3$ becomes the maximum, while the displacement of the P wave component $u_1$ and the displacement of the SV wave component $u_2$ become approximately zero on the surface of the piezoelectric plate 10. Inside the piezoelectric plate 10, the QS mode, in which the SH wave component is larger than the P wave component and the SV wave component, is confirmed (not shown). Furthermore, when m=1, the frequency of the guided wave excited on the piezoelectric plate 10 is f≈9.2 MHz, the wave length is Λ≈597.4 μm, and the electrode finger pitch between the IDT electrode 11 and the IDT electrode 12 is d≈149.3 μm. Besides, by performing a reverse calculation for the approximate values of the multiple roots of $\lambda_3$, $\lambda_4$ from ξh=1.05 and performing a high-order calculation with m=3, 5 (ξh=3.15, 5.25 respectively), the displacement of the P wave component $u_1$ on the surface of the piezoelectric plate 10 becomes larger and the character for the QS mode becomes smaller.

Embodiment 5

Using LGS as the piezoelectric crystalline material, variations of the four roots ($\lambda_1$-$\lambda_4$) of the equation (15) when changing a rotation angle θ around the X-axis of the rotated Y-plate are observed. Ways to define the X-axis, Y-axis and the X-axis are the same as those described in [Embodiment 3]. A physical property of LGS, in which $c_{11}$=1.885×10$^{11}$ [N/m], $c_{66}$=4.221×10$^{10}$ [N/m], $V_L$=5730.8 [m/s], ρ=5739.2 [kg/m³], and $C_{pn}$=1, is assumed. Herein, the physical property of LGS is based on IEEE-176-1949 (R1971) "Standard on Piezoelectricity".

Figure 21:
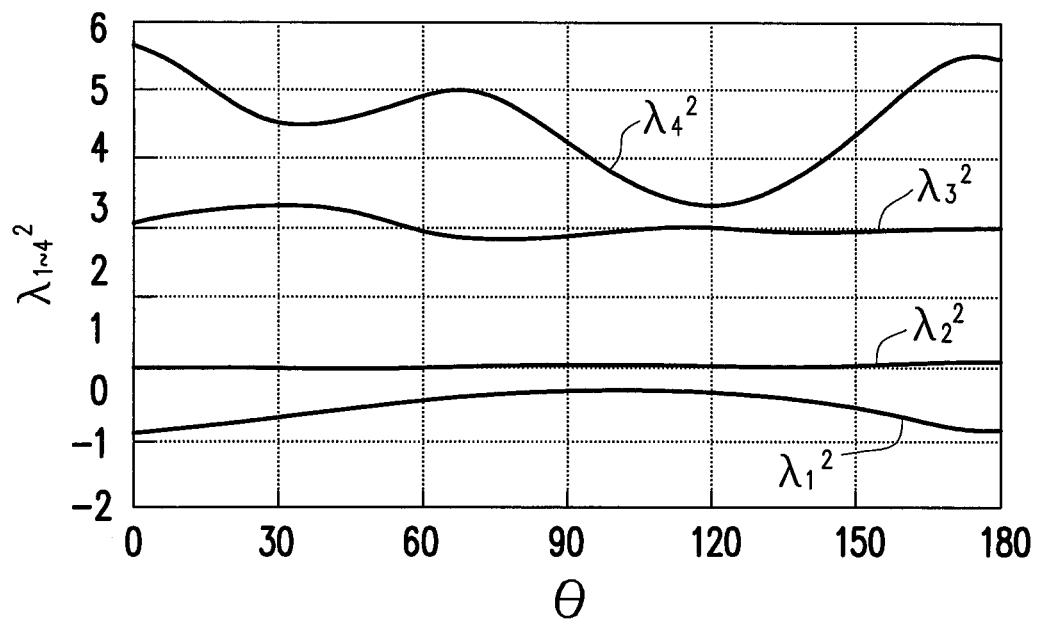
FIG. 21 is an explanatory graph showing root loci of equations of motion when changing a rotation angle around the X-axis on a rotated Y-plate of LGS.

Loci of the roots ($\lambda_1$-$\lambda_4$) of the equation (15) when changing a rotation angle θ of the rotated Y-plate are shown in FIG. 21. FIG. 21 shows squared values of λ in a range of θ=0-180°. According to the results shown in FIG. 21, although two roots of $\lambda_3$ and $\lambda_4$ are adjacent when the rotation angle θ=118°, the difference was much larger than those of LiNbO$_3$ and PZT; therefore, the two roots cannot be considered as multiple roots. However, after dispersion curves (not shown) in the rotation angle are obtained, it is found that the dispersion curves exist when $C_{pn}$ approaches 1 and ξh=1.09, 2.08, so that the guided wave with a frequency corresponding to this $C_{pn}$ can be excited.

Then, by assuming the rotation angle θ=118°, h=100 [μm], ξh=2.08 and m=2 in equation (18), the displacement distributions of the P wave component, the SV wave component and the SH wave component of the guided wave excited in the LGT piezoelectric plate 10 are calculated in considering piezoelectricity. As a result, in a lower order (m=2 in this example), the displacement of the P wave component $u_1$ becomes the maximum, while the displacement of the SV wave component $u_2$ and the displacement of the SH wave component $u_3$ become approximately zero on the surface of the piezoelectric plate 10. Inside the piezoelectric plate 10 as well, the QL mode, in which the P wave component is larger than the SV wave component and the SH wave component, is confirmed. Furthermore, when m=2, the frequency of the guided wave excited on the piezoelectric plate 10 is f≈18.9 MHz, the wave length is Λ≈302.4 and the electrode finger distance between the IDT electrode 11 and the IDT electrodes 12 is d≈75.6 μm. Besides, by performing a reverse calculation for the approximate values of the multiple roots of $\lambda_3$, $\lambda_4$ from ξh=2.08 and performing a high-order calculation with m=4, 6 (ξh=4.16, 6.24 respectively), the displacement of the SH wave component $u_3$ on the surface of the piezoelectric plate 10 becomes larger and the character for the QL mode becomes smaller.

Moreover, in the above-mentioned rotation angle and the half plate thickness h, by assuming ξh=1.09 and m=1 in the equation (18), the displacement distributions of the P wave component, the SV wave component and the SH wave component of the guided wave excited to the LGT piezoelectric plate 10 are calculated in the consideration of piezoelectricity. As a result, in a lower order (m=1 in this example), the displacement of the SH wave component $u_3$ becomes the maximum while the displacement of the P wave component $u_1$ and the displacement of the SV wave component $u_2$ became approximately zero on the surface of the piezoelectric plate 10. Inside the piezoelectric plate 10 as well, the QS mode which the SH wave component is larger than the P wave component and the SV wave component is confirmed (not shown). Furthermore, when m=1, the frequency of the guided wave excited in the piezoelectric plate 10 is f≈9.97 MHz, the wave length is Λ≈574.6 μm, and the electrode finger pitch between the IDT electrode 11 and the IDT electrode 12 is d≈143.7 μm. Besides, by performing a reverse calculation for the approximate values of the multiple roots of $\lambda_3$, $\lambda_4$ from ξh=1.09 and performing a high-order calculation with m=3, 5 (ξh=3.28, 5.46 respectively), the displacement of the P wave component $u_1$ on the surface of the piezoelectric plate 10 becomes larger and the character for the QS mode becomes smaller.

Embodiment 6

Using LGN as the piezoelectric crystalline material, variations of the four roots ($\lambda_1$-$\lambda_4$) of the equation (15) when changing a rotation angle θ around the X-axis of the rotated Y-plate are observed. Ways to define the X-axis, the Y-axis and the Z-axis are the same as those described in [Embodiment 3]. A physical property of LGN is $c_{11}$=1.930×10$^{11}$ [N/m], $c_{66}$=4.116×10$^{10}$ [N/m], $V_L$=5657.8 [m/s], ρ=6028.9 [kg/m$^3$], and $C_{pn}$=1 is assumed. Herein, the physical property of LGN is based on IEEE-176-1949 (R1971) "Standard on Piezoelectricity".

Figure 22:
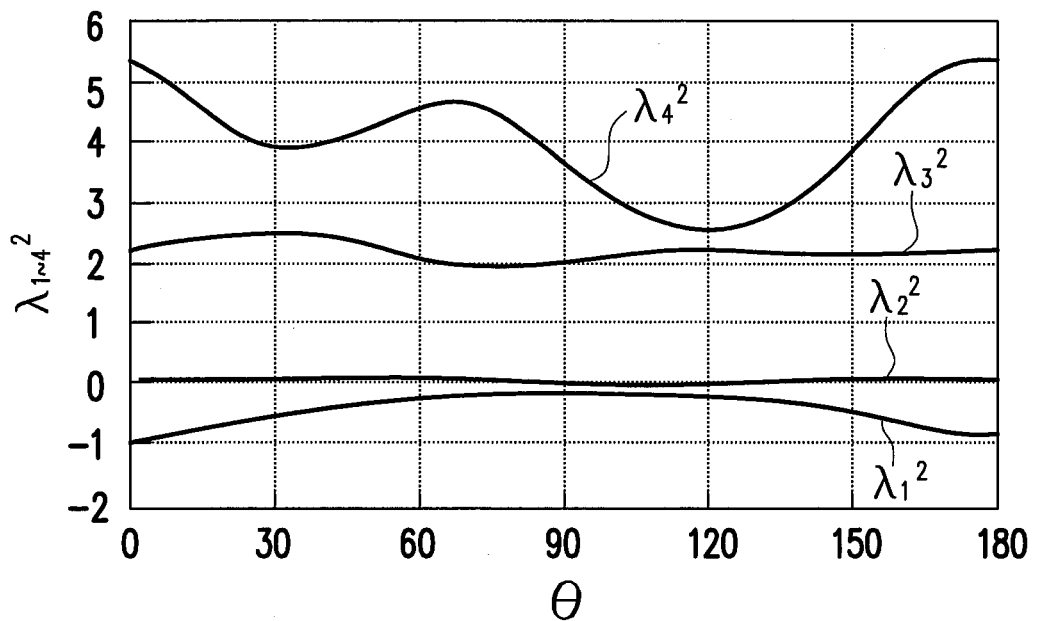
FIG. 22 is an explanatory graph showing root loci of equations of motion when changing a rotation angle around the X-axis on a rotated Y-plate of LGN.

Loci of the roots ($\lambda_1$-$\lambda_4$) of the equation (15) when changing a rotation angle θ of the rotated Y-plate are shown in FIG. 22. FIG. 22 shows squared values of λ within a range of θ=0-180°. According to the results shown in FIG. 22, although two roots of $\lambda_3$ and $\lambda_4$ are adjacent when the rotation angle θ=116°, the difference is much larger than those of LiNbO$_3$ and PZT; therefore the two roots cannot be considered as multiple roots. However, after dispersion curves (not shown) in the rotation angle are obtained, it is found that the dispersion curves exist in the vicinity of $C_{pn}$=1 when ξh=1.05, 1.99, so that the guided wave with a frequency corresponding to this $C_{pn}$ can be excited.

Then, by assuming the rotation angle θ=116°, h=100 [μm], ξh=1.99 and m=2 in the equation (18), the displacement distributions of the P wave component, the SV wave component and the SH wave component of the guided wave excited in the LGN piezoelectric plate 10 are calculated in considerating piezoelectricity. As a result, in a lower order (m=2 in this example), the displacement of the P wave component $u_1$ becomes the maximum, while the displacement of the SV wave component $u_2$ and the displacement of the SH wave component $u_3$ become approximately zero on the surface of the piezoelectric plate 10. Inside of the piezoelectric plate 10 as well, the QL mode, in which the P wave component is larger than the SV wave component and the SH wave component, is confirmed (not shown). Furthermore, when m=2, the frequency of the guided wave excited on the piezoelectric plate 10 is f≈17.9 MHz, the wave length is Λ≈316.4 μm, and the electrode finger pitch between the IDT electrode 11 and the IDT electrode 12 is d≈79.1 μm. Besides, by performing a reverse calculation for the approximate values of the multiple roots of $\lambda_3$, $\lambda_4$ from ξh=1.99 and performing a high-order calculation with m=4, 6 (ξh=3.97, 5.96 respectively), the displacement of the SH wave component $u_3$ on the surface of the piezoelectric plate 10 becomes larger and the character for the QL mode becomes smaller.

Moreover, in the above-mentioned rotation angle and the half plate thickness h, by assuming ξh=1.05 and m=1 in equation (18), the displacement distributions of the P wave component, the SV wave component and the SH wave component of the guided wave excited to the LGN piezoelectric plate 10 are calculated in considerating piezoelectricity. As a result, in a lower order (m=1 in this example), the displacement of the SH wave component $u_3$ becomes the maximum while the displacement of the P wave component $u_1$ and the displacement of the SV wave component $u_2$ become approximately zero on the surface of the piezoelectric plate 10. Also, inside the piezoelectric plate 10, the QS mode, in which the SH wave component is larger than the P wave component and the SV wave component, is confirmed (not shown). Furthermore, when m=1, the frequency of the guided wave excited on the piezoelectric plate 10 is f≈9.24 MHz, the wave length is Λ≈599.2 μm, and the electrode finger pitch between the IDT electrode 11 and the IDT electrode 12 is d≈149.8 μm. Besides, by performing a reverse calculation for the approximate values of the multiple roots of $\lambda_3$, $\lambda_4$ from ξh=1.05 and performing a high-order calculation with m=3, 5 (ξh=3.14, 5.24 respectively), the displacement of the P wave component $u_1$ on the surface of the piezoelectric plate 10 becomes larger and the character for the QS mode becomes smaller.

Embodiment 7

Using $GaPO_4$ as the piezoelectric crystalline material, variations of the four roots ($\lambda_1$-$\lambda_4$) of the equation (15), when a rotation angle θ around the X-axis of the rotated Y-plate changes, are observed. Ways to define the X-axis, Y-axis and the X-axis are the same as those described in [Embodiment 3]. The physical property of $GaPO_4$, in which $c_{11}$=6.658× $10^{11}$ [N/m], $c_{66}$=2.5967×$10^{10}$ [N/m], $V_L$=4318.5 [m/s], ρ=3570 [kg/m³], and $C_{pn}$=1, is assumed.

Figure 23:
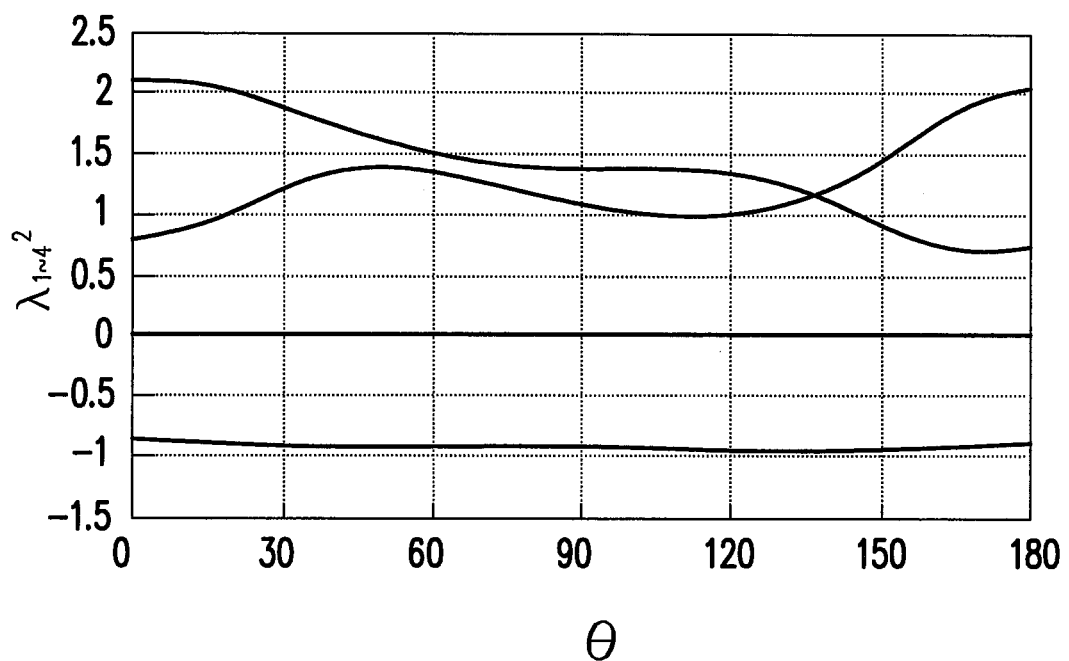
FIG. 23 is an explanatory graph showing root loci of equations of motion when changing a rotation angle around the X-axis on a rotated Y-plate of $GaPO_4$.

Loci of the roots ($\lambda_1$-$\lambda_4$) of the equation (15), when a rotation angle θ of the rotated Y-plate changes, are shown in FIG. 23. FIG. 23 shows squared values of λ in a range of θ=0-180°. According to the results shown in FIG. 23, although two roots of $\lambda_3$ and $\lambda_4$ are adjacent when the rotation angle θ=135.54°, the difference is much larger than those of $LiNbO_3$ and PZT; therefore, the two roots cannot be considered as multiple roots. However, after dispersion curves (not shown) in the rotation angle are obtained, it is found that the dispersion curves exist in the vicinity of $C_{pn}$=1 when ξh=1.43, 2.80, so that the guided wave with a frequency corresponding to this $C_{pn}$ can be excited.

Then, by assuming the rotation angle θ=135.54°, h=100 [µm], ξh=2.80 and m=2 in equation (18), the displacement distributions of the P wave component, the SV wave component and the SH wave component of the guided wave excited to the $GaPO_4$ piezoelectric plate 10 are calculated in considering piezoelectricity. As a result, in a lower order (m=2 in this example), the displacement of the P wave component $u_1$ becomes the maximum while the displacement of the SV wave component $u_2$ and the displacement of the SH wave component $u_3$ become approximately zero on the surface of the piezoelectric plate 10. Inside the piezoelectric plate 10, the QL mode, in which the P wave component is larger than the SV wave component and the SH wave component, is confirmed (not shown). Furthermore, when m=2, the frequency of the guided wave excited on the piezoelectric plate 10 is f≈19.3 MHz, the wave length is Λ≈224.0 µm, and the electrode finger pitch between the IDT electrodes 11 and 12 is d≈56.0 µm. Besides, by performing a reverse calculation for the approximate values of the multiple roots of $\lambda_2$, $\lambda_3$ from ξh=2.80 and performing a high-order calculation with m=4, 6 (ξh=5.61, 8.41 respectively), in these high order as well, the QL mode, in which the P wave component becomes the maximum while the SV wave and the SH wave components become smaller on the surface of the piezoelectric plate 10, is confirmed.

Moreover, in the above-mentioned rotation angle and the half plate thickness h, by assuming ξh=1.43 and m=1 in equation (18), the displacement distributions of the P wave component, the SV wave component and the SH wave component of the guided wave excited to the $GaPO_4$ piezoelectric plate 10 are calculated in considering piezoelectricity. As a result, in a lower order (m=1 in this example), the displacement of the SH wave component $u_3$ becomes the maximum, and the displacement of the P wave component $u_1$ and the displacement of the SV wave component $u_2$ become approximately zero on the surface of the piezoelectric plate 10. Inside the piezoelectric plate 10, the QS mode, in which the SH wave component is larger than the P wave component and the SV wave component, is confirmed (not shown). Furthermore, when m=1, the frequency of the guided wave excited on the piezoelectric plate 10 is f≈9.82 MHz, the wave length is Λ≈439.8 µm, and the electrode finger pitch between the IDT electrode 11 and the IDT electrode 12 is d≈110.0 µm. Besides, by performing a reverse calculation for the approximate values of the multiple roots of $\lambda_2$, $\lambda_3$ from ξh=1.43 and performing a high-order calculation with m=3, 5 (ξh=4.28, 7.14 respectively), in these high order as well, the QS mode, in which the SH wave component becomes the maximum while the P wave and the SV wave components become smaller on the surface of the piezoelectric plate 10, is confirmed.

What is claimed is:

1. A piezoelectric sensor, comprising:
   a piezoelectric plate, obtained from a rotated Y-plate having a rotation angle θ around an X-axis, wherein when at least a two-fold symmetry axis, or a symmetry axis of a piezoelectric crystalline material having a mirror symmetry plane is set as the X-axis, and the rotation angle θ is set according to a type of the piezoelectric crystalline material;
   a detection region located on a surface parallel to an X-Z plane of the piezoelectric plate; and
   a transmitting part and a receiving part, located along a direction of the X-axis of the piezoelectric plate and opposite to each other at positions that sandwich the detection region,
   wherein when a guided wave excited in the piezoelectric plate by applying a frequency signal from the transmitting part satisfies an equation (A) below, the rotation angle θ satisfies:
   (a1) the guided wave propagating in the direction of the X-axis inside the piezoelectric plate has a P wave component, an SV wave component and an SH wave component;
   (b1) when a displacement of the P wave component is $u_1$, a displacement of the SV wave component is $u_2$ and a displacement of the SH wave component is $u_3$, the displacement $u_1$ becomes the maximum, and the displacements $u_2$ and the $u_3$ become less than 10% of the displacement $u_1$ on the surface according to a following equation (1), $$\xi h = m\pi/(2\lambda) \tag{A}$$

$$u_i = A_i \exp j(\lambda \xi x_2) \exp j(\xi x_1 - \omega t), \ i=1, 2 \text{ and } 3 \tag{1}$$

where 2h is a plate thickness of the piezoelectric plate, ξ is a wave number in the X-axis direction, λ is a wave number in a plate thickness direction normalized by ξ, m is a positive even number to make a QL mode excited, $x_2$ is a coordinate in Y-axis direction, $x_1$ is a coordinate in the X-axis direction, and ω is an angular frequency, and $A_i$ is an amplitude ratio of a displacement of a wave corresponding to $\lambda_i$.

2. The piezoelectric sensor as claimed in claim 1, wherein the transmitting part and the receiving part are Inter-digital transducer (IDT) electrodes, wherein an electrode finger pitch d is defined by the following equation (C)

$$d = (2\pi h/\xi h)/4 \tag{C}$$

3. The piezoelectric sensor as claimed in claim 1, wherein the piezoelectric crystalline material is lead zirconate titanate.

4. The piezoelectric sensor as claimed in claim 1, wherein the piezoelectric crystalline material is lithium niobate.

5. The piezoelectric sensor as claimed in claim 1, wherein the piezoelectric crystalline material is selected from a langasite-type piezoelectric crystalline material group consisting of Al-substituted langatate, langatate, langasite and langanite.

6. The piezoelectric sensor as claimed in claim 1, wherein the piezoelectric crystalline material is gallium phosphate.

7. The piezoelectric sensor as claimed in claim 1, wherein the piezoelectric sensor is a sensing sensor where an adsorption layer to adsorb a sensing object is disposed on the detection region.

8. The piezoelectric sensor as claimed in claim 1, wherein the piezoelectric sensor is a viscosity sensor for detecting a viscosity change of a fluid contacting with the detection region.

9. A piezoelectric sensor, comprising:
a piezoelectric plate, obtained from a rotated Y-plate having a rotation angle θ around an X-axis, wherein when at least a two-fold symmetry axis, or a symmetry axis of the piezoelectric crystalline material having a mirror symmetry plane is set as the X-axis, and the rotation angle θ is set according to a type of the piezoelectric crystalline material;
a detection region located on a surface parallel to an X-Z plane of the piezoelectric plate; and
a transmitting part and a receiving part, located along a direction of the X-axis of the piezoelectric plate and opposite to each other at positions that sandwiches the detection region,
wherein when a guided wave excited in the piezoelectric plate by applying a frequency signal from the transmitting part satisfies an equation (B) below, the rotation angle θ satisfies:
(a2) the guided wave propagating in the direction of the X-axis of the piezoelectric plate has a P wave component, an SV wave component and an SH wave component;
(b2) when a displacement of the P wave component is $u_1$, a displacement of the SV wave component is $u_2$ and a displacement of the SH wave component is $u_3$, the displacement $u_3$ becomes maximum, and the displacement $u_1$ becomes less than 10% of the displacement $u_3$ on the surface according to a following equation (1), $$\xi h = m\pi/(2\lambda) \tag{B}$$

$$u_i = A_i \exp j(\lambda \xi x_2) \exp j(\xi x_1 - \omega t), i=1, 2 \text{ and } 3 \tag{1}$$

where 2h is a plate thickness of the piezoelectric plate, $\xi$ is a wave number in the X-axis direction, $\lambda$ is a wave number in a plate thickness direction normalized by $\xi$, m is a positive odd number to make a QS mode excited, $x_2$ is a coordinate in Y-axis direction, $x_1$ is a coordinate in the X-axis direction, and ω is an angular frequency, and $A_i$ is an amplitude ratio of a displacement of a wave corresponding to $\lambda_i$.

10. The piezoelectric sensor as claimed in claim 9, wherein the transmitting part and the receiving part are IDT electrodes, and an electrode finger pitch d is defined by the following equation (C)

$$d=(2\pi h/\xi h)/4 \tag{C}$$

11. The piezoelectric sensor as claimed in claim 9, wherein the piezoelectric crystalline material is lead zirconate titanate.

12. The piezoelectric sensor as claimed in claim 9, wherein the piezoelectric crystalline material is lithium niobate.

13. The piezoelectric sensor as claimed in claim 9, wherein the piezoelectric crystalline material is selected from a langasite-type piezoelectric crystalline material group consisting of Al-substituted langatate, langatate, langasite and langanite.

14. The piezoelectric sensor as claimed in claim 9, wherein the piezoelectric crystalline material is gallium phosphate.

15. The piezoelectric sensor as claimed in claim 9, wherein the piezoelectric sensor is a sensing sensor where an adsorption layer to adsorb a sensing object is disposed on the detection region.

16. The piezoelectric sensor as claimed in claim 9, wherein the piezoelectric sensor is a viscosity sensor to detect a viscosity change of a fluid contacting with the detection region.

* * * * *